United States Patent [19]

Malfroy-Camine et al.

[11] Patent Number: 5,780,025
[45] Date of Patent: Jul. 14, 1998

[54] COMPOSITIONS AND METHODS FOR THE SYNTHESIS AND ASSAY OF ENKEPHALINASE

[75] Inventors: Bernard Malfroy-Camine, San Bruno; Peter R. Schofield, San Francisco, both of Calif.

[73] Assignee: Genentech, Inc., So. San Francisco, Calif.

[21] Appl. No.: 134,481

[22] Filed: Oct. 12, 1993

Related U.S. Application Data

[63] Continuation of Ser. No. 540,439, Jun. 19, 1990, abandoned, which is a continuation of Ser. No. 2,478, Jan. 12, 1987, Pat. No. 4,960,700, which is a continuation-in-part of Ser. No. 946,566, Dec. 24, 1986, abandoned.

[51] Int. Cl.$^6$ .............................. A61K 38/48; C12N 9/48
[52] U.S. Cl. ................................ 424/94.67; 435/212
[58] Field of Search ...................... 435/212; 424/94.67

[56] References Cited

U.S. PATENT DOCUMENTS 5,262,178  11/1993  Malfroy-Camine et al. ........ 424/94.67

OTHER PUBLICATIONS

Malfroy et. al. (1984) J. Biol. Chem. 259, 14365–14370.
Gafford et. al. (1983) Biochem. 22, 3265–3271.
Kalyan et. al. (1983) J. Biol. Chem. 258, 67–74.
Almenoff et al., Biochemistry 22:590–599 (1983).
Tonouchi et al., Nucleic Acids Res. 14:7557–7568 (1986).
Treiger et al., J. Immunol. 136:4099–4105 (1986).
Skidgel et al., Peptides 5:769–776 (1984).
Bleecker et al., Amer. J. Med. 81(5A):93–102 (1986).
Kerr, M.A., et al., "The Purification and Specificity of a Neutral Endopeptidase from Rabbit Kidney Brush Border," Biochem. J., 137:477–488 (1974).

Primary Examiner—Eric Grimes
Attorney, Agent, or Firm—Flehr Honbach Test Albritton & Herbert LLP; David J. Brezner; Robin M. Silva

[57] ABSTRACT

DNA isolates coding for enkephalinase and methods of obtaining such DNA are provided, together with expression systems for recombinant production of enkephalinase for use in therapeutic or diagnostic compositions. Enkephalinase assays are facilitated by novel enkephalinase substrates.

20 Claims, 17 Drawing Sheets

```
                    1                                                        10
        LYS SER GLU SER GLY LEU MET ALA SER PRO ILE LEU THR ASP PRO LYS SER ASN THR PRO
   1    GCA AGT CAG AAA GTC AGA TGG ATA ACT CAA CAC TCC AAA GCC AAA GAA GAA CAG CGA TGG ACT CCA 20                                                30                                         40
        LEU GLU LEU ILE GLU SER ARG LEU VAL LEU GLU VAL LEU GLU LEU THR HIS ILE LEU ILE GLU ALA LEU ALA VAL THR HIS ARG MET GLU THR ILE LEU GLU ALA LEU ALA LEU GLU THR TYR ARG ALA THR
  75    CTG GAG ATC AGC CTC TCG GTT CCT TGT CTC CTG CTC CTG CTC CTG CTG TCC TGC TCC ACC ATC ATA GCT GTG ACA CAT CGC CAC TCT ATG CAA CC 50                                          60
        TYR ARG ASP ALA SER PRO GLY LEU ILE GLU CYS ILE LEU LYS SER SER LEU LYS SER SER SER GLU ARG ALA SER PRO CYS SER ILE LEU GLU LEU TYR LYS SER SER GLU ARG ALA LEU ALA LEU ALA ARG GLY LEU ILE LEU GLU GLN LEU ASN MET GLU THR ALA SER PRO ALA LEU THR
  150   TAC GAT GAT GGT ATT TGC AAG TCA TCA GAC TCA GAA GTC AGA AGT CAT CAG ACT GCA TAA AAT CAG CTG CTC GAC TGA TCC AAA ACA TGG ATG CCA CC 70                                                80                                           90
        THR ARG GLU PRO CYS THR HIS ARG ALA SER PRO PHE PRO HIS GLU LEU LYS SER TYR ARG ALA CYS SER GLY LEU TYR GLY LEU TYR THR ARG PRO LEU GLU LEU TYR LYS SER ARG GLY ALA SER ASN VAL ALA LEU ILE PRO GLY LEU THR ARG SER
  225   ACT GAG CCC TGT ACA GAC TTT GTA CAG ACT TTT CAA ATA TCT TGC GGA GGC TGG TGG TGG TGG TTA TCG CGG GTA TAC AGG TCT GAT GTC ATT CCC GAG ACC AGC

110
        SER GLU ARG GLY TYR ARG GLY LEU TYR ALA ASN PHE GLU ALA SER PRO ILE LEU GLU LEU ARG GLY ALA SER PRO GLY LEU GLU LEU GLY LEU VAL ALA LEU VAL ALA LEU LEU LYS SER ALA SER PRO VAL ALA LEU GLU LEU GLY LEU ASN GLY LEU PRO GLY LEU LYS SER
  300   TCC CGG TTA CGG GCA ACT TTG ACA TTT GAC ATA TTT AAG AGA GCA TTT AAG AGA GCA TTT GAC ATA TTT CAA ATG GCC AAG GCC AAG CCG AAC CCA AAA 130                                           140
        THR GLU LEU ALA SER PRO ILE LEU GLU VAL ALA LEU ALA LEU ALA VAL ALA LEU GLY LEU ASN LYS SER ALA LEU ALA LEU TYR SER ALA LEU ALA LEU GLU LEU TYR ARG ALA ARG GLY SER GLN CYS SER ILE LEU GLU ALA SER ASN GLU SER ALA ILE LEU GLU ALA SER PRO SER
  375   ACT GAA GAT ATA GTA GCA GTG CAG AAG CAG AAA GCA AAG TCA GGT CTC TGT ATA AAT GAA TCG TAT TGA TAG C

160
        ARG GLY LEU TYR GLY LEU GLU PRO ARG LEU GLU LEU TYR SER LEU GLU LEU PRO ARG ASP PRO ILE LEU GLU THR TYR ARG GLY LEU TYR ARG PRO PRO VAL ALA LEU ALA LEU THR ARG GLU LEU ASN THR ARG PRO GLY LEU GLU GLN LEU ASN
  450   AGA GGG GGA GAA CCT CTA CTC AAA CTG TTA CCA GAG ATA TAT GGG TGG CCA GTA GCA ACA GAA AAC TGG GAG CAA 170                                           180                                           190
        LYS SER TYR ARG GLY LEU TYR ALA LEU ALA SER GLU ARG TRP PRO THR HIS ARG ALA LEU ALA GLY LEU LEU LYS SER ALA LEU ALA ILE LEU GLU ALA LEU ALA GLY LEU ASN LEU GLU ALA SER ASN SER GLU ARG LYS SER TYR ARG GLY LEU TYR LEU TYR SER VAL ALA LEU LEU ILE LEU GLU
  525   AAA TAT GGT GCT TCT TGG ACA GCT GGA AAA AGC TAT TGC ACA ACT GAA TTC TAA ATT GGG AAA AAG TCC TTA TT
```

*FIG._1a*

```
          200
     ASNLEUPHEVALGLYTHRASPASPLYSASNSERVALASNHISVALILEHISILEASPGLNPROARGLEUGLYLEU
                                      210
600  AATTTGTTTGTTGGCACTGATGATAAGAATTCTGTGAATCATGTAATTCATATTGACCAACCTCGACTTGGCCTC
          220
     PROSERARGASPTYRTYRGLUCYSTHRGLYILETYRLYSGLUALACYSTHRALATYRVALASPPHEMETILESER
                                      230                                 240
675  CCTTCTAGAGATTACTATGAATGCACTGGAATCTATAAAGAGGCTTGTACAGCATATGGATTTTATGATTTCT
          250
     VALALAARGLEUILEARGGLYLEUGLULEUPROILEASPGLUASNGLNLEUALALEUGLUMETASNLYSVAL
                                      260
750  GTGGCCAGATTCGTCAGGAGAAGAGATTGCCCATCGATGAAAACCAGCTTGCTTTGGAAATGAATAAAGTT
          270
     METGLULEUGLULYSGLUILEALAGLUALAASNALATHRALALYSPROGLUASPARGASNASPPROMETLEULEUTYRASN
                                      280                                 290
825  ATGGAATTGGAAAAAGAAATCATGTCAACTGCTAAACCTGAAGATCGAAATGATCCAATGCTTCTGTATAAC
          300
     LYSMETTHRLEUALAGLNILEGLNASNASNPHESERLEUGLULLEASNGLYLYSPROPHESERTRPLEUASNPHE
                                      310
900  AAGATGACACTGGCCCAGATTCAGAATAACTTTTCACTAGAGAATCAATGGGAAGCCATTCAGCTGGTTGAATTC
          320
     THRASNGLUILEMETSERTHRVALASNILESERILETHRASNGLULGLUASPVALVALVALTYRALAPROGLUTYR
                                      330                                 340
975  ACAAATGAAATCATGTCAACTGTGAATATTAGTATTACAAATGAGGAAGATGTGGTTGTTGTTTATGCTCCAGAATAT
          350
     LEUTHRLYSLEULYSPROILELEUTHRLYSTYRSERALAARGASPLEUGLNASNLEUMETSERTRPARGPHEILE
                                      360
1050 TTAACCAAACTTAAGCCCATTCTAACCAAATATTCTGCCAGAGATCTTCAAAATTTAATGTCCTGGAGATTCATA
          370
     METASPLEUVALSERSERLEUSERARGTHRTYRLYSGLUSERARGASNALAPHEARGLYSALALEUTYRGLYTHR
                                      380                                 390
1125 ATGGATCTTGTAAGCAGCCTCAGCGACCGAACCTACAAGGAGTCCAGAAATGCTTTCCGCAAGGCCCTTTATGGTACA
```

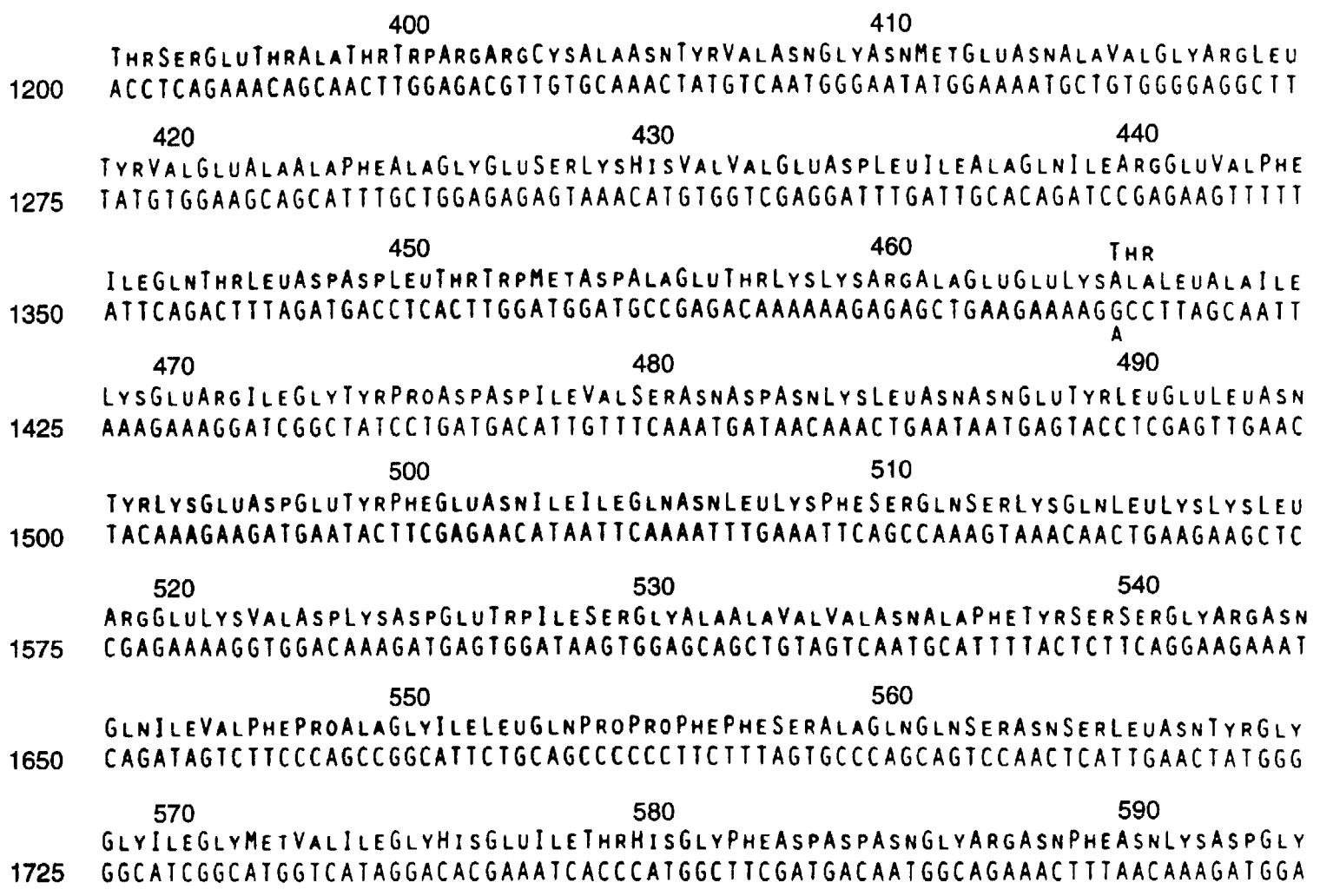

```
                    600
     ASPLEUVALASPTHRPTRPTHRGLUGLNGLUGLNSERALASERASNPHELYSGLUGLNSERGLNCYSMETVALTYRGLNTYR
1800 GACCTCGTTGACTGGTGGACTGGACTCAACAGTCTGCAAGTAACTTAAGGAGCAATCCCAGTGCATGGTGTATCAGTAT
                    620                                                      640
     GLYASNPHESERTRPASPLEUALAGLYLYGLYLYGLNHISLEUASNTHRLEUGLYLEUGLYGLUASNILEALAASP
1875 GGAAACTTTTCCTGGGACCTGGCAGGTGGACAGCAGGACACCTTAATGGAATTAATACACTGGGAGAAACATTGCTGAT
                    650                                                      660
     ASNGLYGLYLEUGLYGLNALALATYRARGALALATYRGLNASNTYRILELELYSLYSASNGLYLYGLULYSLEULEUPRO
1950 AATGGAGGTCTTGGTCAAGCATACAGAGCCTATCAGAATTATATTAAAAAGAATGGCGAAGAAAATTACTTCCT
                    670                                                      690
     GLYLEUASPLEUASNHISLYSGLNLEUPHEPHELEUASNPHEALAGLNVALTRPCYSGLYTHRTYRARGPROGLU
2025 GGACTTGACCTAAATCACAAATCAACTATTTTCTTGAACTTTGCACAGGTGTGGTGTGTGGAACTATAGGCCAGAG
                    700                                                      710
     TYRALAVALASNSERILELYSTHRASPVALHISSERPROGLYASNPHEARGILEILEGLYTHRLEUGLNASNSER
2100 TATGCGGTTAACTCCATTAAAACAGATGTGCACAGTCCAGGCAATTTCAGGATTATTGGGACTTTGCAGAACTCT
                    720                                                      740
     ALAGLUPHESERGLUALAPHEHISCYSARGLYSASNSERTYRMETASNPROGLULYSLYSCYSARGVALTRPOP*
2175 GCAGAGTTTTCAGAAGCCCTTCACTGCCGCAAGAAATCCAAGAATTCATACATGAATCCAGAAAAGAAGTGCCGGGTTTGGTGA

2250 TCTTCAAAAGAAGCATTGCAGCCCTTGGCTAGACTTGAGGGTGACTTGAGGGTGATTAACAGAGAGGGCACCATCACAATACAGATAACAT

2325 AAATGGGCCCTAGGGGTCACTGTACTGACTTGAGGGTGATTAACAGAGAGGGCACCATCACAATACAGATAACAT

2400 TAGGTTGTCCTAGAAAGGGTGTGGAGGAGGAAGGGGGTCTAAGGTCTATCAAGTCAATCATTCTCACTGTGTA

2475 CATAATGCTTAATTTCTAAAGATAATATTACTGTTTATTTCTGTTTCTCATATGGTCTACCAGTTTGCTGATGTC
```

FIG._1d

| | |
|---|---|
| 2550 | CCTAGAAAACAATGCAAAACCTTTGAGGTAGACCAGGATTTCTAATCAAAAGGGAAAAGAAGATGTTGAAGAATA |
| 2625 | CAGTTAGGCACCAGAGAAGAACAGTAGGTGACACTATAGTTTAAAACACATTGCCTAACTACTAGTTTTACTTTTA |
| 2700 | TTTGCAACATTTACAGTCCTTCAAAATCCTTCCAAAGAATTCTTATACACATTGGGGCCTTGGAGCTTACATAGT |
| 2775 | TTTAAACTCATTTTTGCCATACATCAGTTATTCATTCTGTGATCATTTATTTTAAGCACTCTTAAAGCAAAAAAT |
| 2850 | GAATGTCTAAAATTGTTTTTGTTACCTGCTTTGACTGATGCTGAGATCTTCAGGCTTCCTGCAATTTTCTA |
| 2925 | AGCAATTTCTTGCTCTATCTCTCAAAACTGGTATTTTCAGAGATTTATATAAATGTAAAAATAATTTTTA |
| 3000 | TATTTAATTATTAACTACATTTATGAGTAACTATTATTATAGGTAATCAATGAATATTGAAGTTTCAGCTTAAAA |
| 3075 | TAAACAGTTGTGAACCAGATCTATAAAGCGATATACAGATGAAAATTTGAGACTATTTAAACTTATAAATCATA |
| 3150 | TTGATGAAAAGATTTAAGCACAAACTTTAGGG |

*FIG._1e*

```
  1  GCGGAGATGTGCAAGTGGGCGAAGCTGGACCGAGTGCAGGGCGCAAGCTGCTGAGCGGGCTGAGGCGGAGGGATTTTAG
                                                              10
        MetGlyArgSerGlnMetAspIleThrAspIleAsnAlaProLysLysProLysLysGlnArgTrp
 76  GTGATGGGCAAGTCAGAGATCAGAAGTCAGATCCAAAGCCGAAGAAGAAACAGGCGATGG
                  20                      30                       40
       ThrProLeuGluIleSerLeuSerValLeuLeuThrIleIleAlaValThrMetIleAlaLeuTyr
151  ACTCCACTGGAGATCAGCCTTTCTGTGCTCCTGACTATCATAGCTGTGACAATGATTGCTCTCTAT
                      50                         60
       AlaThrTyrAspAspGlyIleCysLysLysSerSerAspCysIleIleGlnAsnMetAsp
226  GCAACCTATGATGATGGTATTTGCAAATCATCAGACTGCTCTGATCCAGAACATGGAT
                      70                         80                       90
       AlaSerAlaGluProCysThrAspPhePheLysTyrAlaCysGlyGlyTrpLeuLysArgAsnValIleProGlu
301  GCCTCTGCTGAGCCATGTACGGACTTCTTCAAATATGCTTGTGGAGGCTGGTTGAAACGCAATGTCATCCCTGAG
                     100                       110
       ThrSerSerArgTyrSerAsnPheAspIleLeuArgAspGluLeuLysAspValLeuGlnGlu
376  ACCAGTTCCAGATACAGTAATTTTGACATTCTAAGAGATGAACTAAAGATGTCCTTGAAGAA
                     120                       130                      140
       ProLysThrGluAspIleValAlaValGlnLysAlaAlaLysThrLeuTyrArgSerCysIleAsnGluSerAlaIle
451  CCCAAAACTGAGGACATAGTAGCAGTGCAGAAAGCAAAAACTTTGTACAGATCATGTATAAATGAATCTGCTATT
                     150                      160
       AspSerArgGlyGlyGlnProLeuLeuThrLeuLeuProAspIleTyrGlyTrpProValAlaSerGlnAsnTrp
526  GATAGCAGAGGTGGGCAACCTCTGCTCACACTGTTACCAGATATATATGGGTGGCCAGTAGCATCACAAAACTGG
```

FIG._2a-1

```
                                    180                                              190
      GluGlnThrTyrGlyThrSerTrpThrAlaGluLysSerIleAlaGlnLeuAsnSerLysTyrGlyLeuLysVal
  601 GAACAAACATATGGTACTTCTTGGACAGCTGAGAAATCTATTGCACAACTGAATTCTAAATATGGGAAAAAGGTC
                    200                                    210
      LeuIleAsnPhePheValGlyThrGlyThrGlnHisIleIleHisPheAspGlnProArgLeu
  676 CTCATTAATTTTTTTGTTGGCACTGGTACTCAGCATATAATTCATTTTGACCAGCCTCGACTT
                                    220                                    230
      GlyLeuProSerArgAspTyrTyrGluCysThrGlyIleTyrLysGluAlaCysThrAlaTyrValAspPheMet
  751 GGCCTCCCTTCCAGAGACTACTATGAGTGTACAGGAATATATAAAGAGGCTTGCACAGCATATGTGGATTTTATG
                              240                                          250
      IleSerValAlaArgLeuIleArgGlnGluAsnGlnLeuProIleAspGluAsnGlnLeuMetAsn
  826 ATTTCTGTGGCCAGACTGATTCGTCAGGAACAAAAGATTGCCTATTGATGAAAACCAGTCTCTTTGGAAATGAAT
                    270                                    280                290
      LysValMetGluLeuGluLysGluIleAlaAsnAlaThrLysProGluAspArgAsnAspProMetLeuLeu
  901 AAAGTTATGGAATTGGAAAAAGAAATTGCCACAACCAGAGACCGAAATGACCAATGCCGCTT
                    300                                    310
      TyrAsnLysMetThrLeuAlaLysGlnLeuAsnAsnPheSerLeuGluIleAsnGlyLysProPheSerTrpSer
  976 TATAACAAAATGACATTGGCCAAGCTCCAAAATAACTTCTCTCTGGAGATCAATGGGAAGCCATTCAGCTGGTCA
                              320                                          330                340
      AsnPheThrAsnGluIleMetSerThrValAsnIleGlnAsnGluGluValValValTyrAlaPro
 1051 AATTTCACAAATGAAATCATGTCAACTGTGAATATTCAAAATGAGGAAGAAGTGGTTGTTTATGCTCCA
                    350                                              360
      GluTyrLeuThrLysLeuLysProIleLeuThrLysTyrSerProArgAspLeuGlnAsnLeuMetSerTrpArg
 1126 GAATATTTAACCAAACTTAAGCCTATTCTTACCAAATACTTCCCAGAGATCTTCAAAATTGTCCTGGAGG
```

FIG._2a-2

```
                              370                       380                                390
          PheIleMetAspLeuValSerSerLeuSerArgArgAsnTyrLysGluSerArgAsnAlaPheArgLysAlaLeuTyr
1201      TTCATAATGGATCTTGTAAGCAGCCTCAGCCGAAGAAGGAGTCCAGAAACTACAAGGAGTCCAGAAATGCTTTCCGCAAGGCCCTTTAC 400                       410
          GlyThrThrSerGluThrAlaThrTrpArgArgCysAlaAsnTyrValAlaAsnGlyAsnMetGluAsnAlaValGly
1276      GGGACTACATCCGAAACTGCAACCTGGAGACGGGTGTGCCAACTACGTCAATGGGAACATGGAGAATGCTGTGGGG 420                       430                                440
          ArgLeuTyrValGluAlaAlaAlaPheAlaGlyGluSerLysHisValValGluAspLeuIleAlaGlnIleArgGlu
1351      AGGCTTTATGTGGAAGCAGCTTTTGCTGGAGAGAGCAAGCACGTGGTTGAAGATTTGATTGCACAAATCCGTGAA 450                       460
          ValPheIleGlnThrLeuAspAspLeuThrTrpMetAspLeuThrLysLysLysAlaGluGluLysAlaLeu
1426      GTTTTATTCAGACTTTAGATGACCTCACTTGGATGCTGAGACAAAAAGAAGCTGAAGAGAAGGCCCTG 470                       480                                490
          AlaIleLysGluArgIleGlyTyrProAspAspIleIleSerAsnGluAsnLysLeuAsnAsnGluTyrLeuGlu
1501      GCAATTAAAGAAAGGATTGGCTATCCTGATGACATCATCTCCAATGAGAATAAACTGAATAATGAGTATCTTGAG 510                       520
          LeuAsnTyrLysGluGluTyrPheGluAsnIleIleGlnAsnLeuLysPheSerGlnSerLeuLys
1576      TTGAACTACAAGGAAGAGTACTTTGAGAACATAATTCAAAATTGAAATTCAGCCAAAGCAAGCAGCTAAAG 530                       540
          LysLeuArgGluLysValAspLysAspGluTrpIleSerGlyAlaAlaValAlaAsnAlaPheTyrSerSerGly
1651      AAGCTCCGAGAAAAGGTGGACAAAGATGAGTGGATAAGTGGCGCGGTAGTAGCAAATGCATTTTATTCCTCAGGC 550                       560
          ArgAsnGlnIleValPheProAlaGlyIleLeuGlnProProPhePheSerAlaArgGlnSerAsnSerLeuAsn
1726      AGAAATCAGATCGTCTTCCCCGCCATTTTGCAGCCCCCATTCTTTAGTGCTCGGCAGTCCAACTCATTGAAC
```

```
TrpOP*
2326  TGGTGATCTTCACAGGAAGTGGAGCATCCATGGCAGGACTGCGCCAAAGCCACAGAAACAGGAAGTCTTCCCTCAG
2401  AGAACGTGGGCCCCGGAAGTTCTTCAGCTTTCTTGGGGAAATTCACAGAGATGAGCACGAGCTAACAAAATGA
2476  AATTAGATTATTAAAACCGCTGTGAATGAAAGGGAGAAAACCTACGATCTAGCAAATCAATCACTTCACTGTGT
2551  AAATAATTACCTTCCAACGGTAACTTAAAGCAGGTTATGACTTCTGATCAAGAGGAAGACGCTGAATACAGTTGGGC
2626  TAGAGAACAGTGTTAACACTTAAAGCAGGTTATGACTTCTGATCAAGAGGAAGACGCTGAATACAGTTGGGC
2701  ACCAAAGTACAGATTGCCTCTCAGCACTCACTTTGTTTGCAACATTCAGCTCCTTCAAAATTCTCCAAAGAA
2776  CCCCCATGCATACTGTGGCCCTTCAGGCTCCTGCAGTGTGGAACTCATTTTACCATGCATAAATTATTCATT
2851  CCACATCATTTAGTTTGAGCACTCTTAGAGCTTAAACTAGAGAGTCTGAAATGGTTCCGCCATTACCCACTTG
2926  AGTGGTGTTGAGACTCTTCAGCCCCCTACAGATTTTGAGCAATTTCTTGCTCCGTCGCTGCCCCCTCAGACTTAGTC
      A
3001  TTTTAAAGGATTTGTAGTAATGTATAAAAACATTCTATATTTAATTATTAACTACACATGACCAAATAAACCAT
3076  TGCTATAGGTAATCATTGAATATTGACATTATATGGCCAAGATAGAGATAGTTAAGAAGATCTGTAACATGATGTGC
3151  AGATGAAAATTTGAAACTTTTTAAGCCTGTAAATCATATTGCTGAAAATCATATTGCTGAAATCATATTGGGGTGAGC
3226  ATTACCATTGAACAGTTG
```

FIG._2a-5

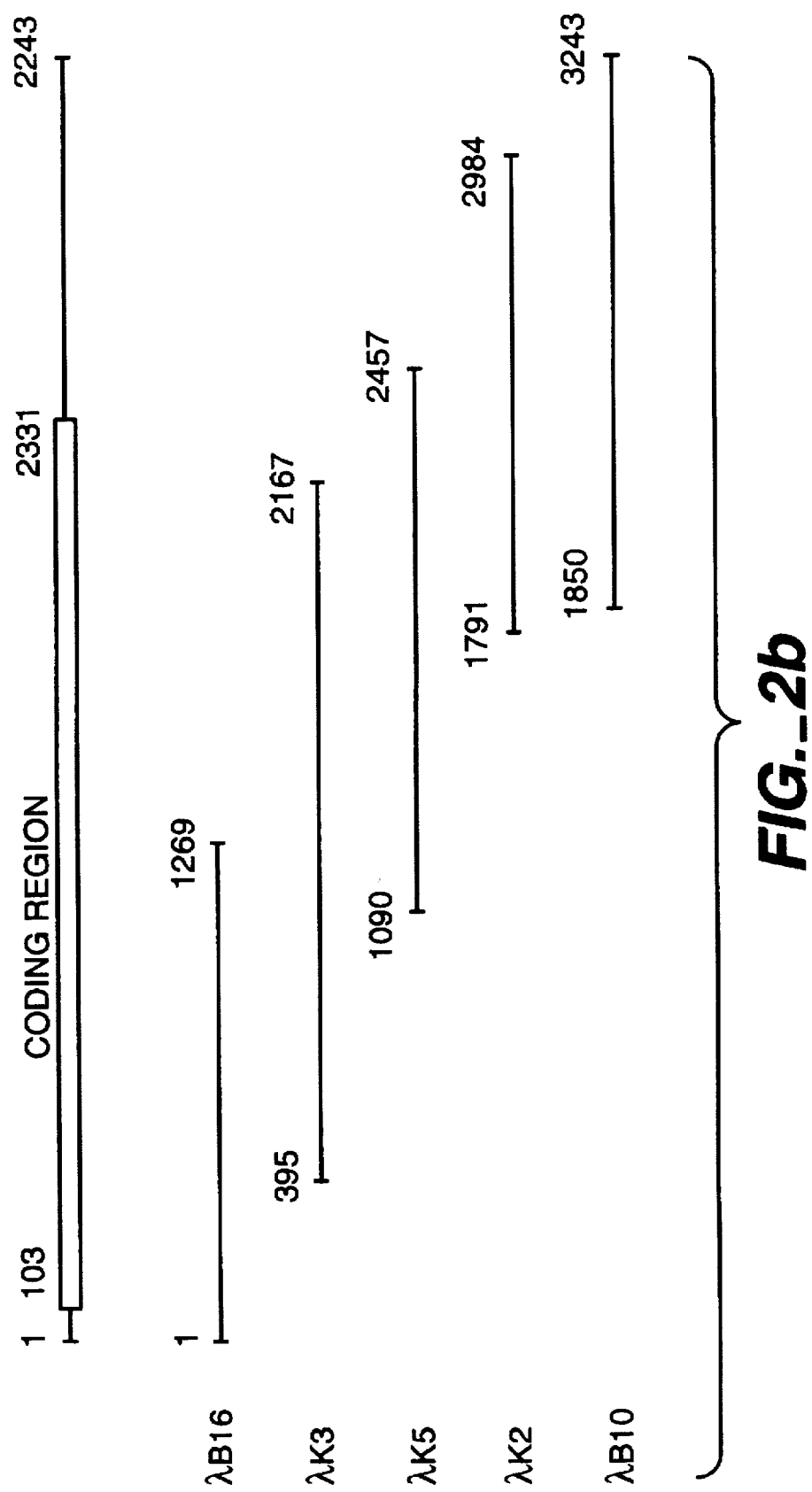
FIG._2b

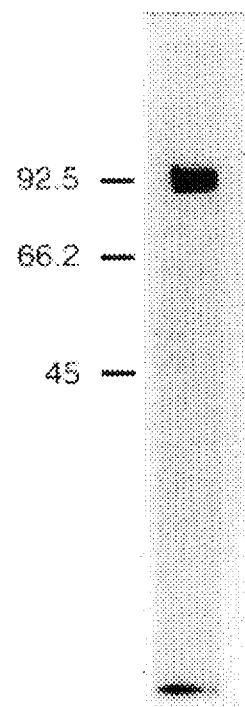
FIG._3

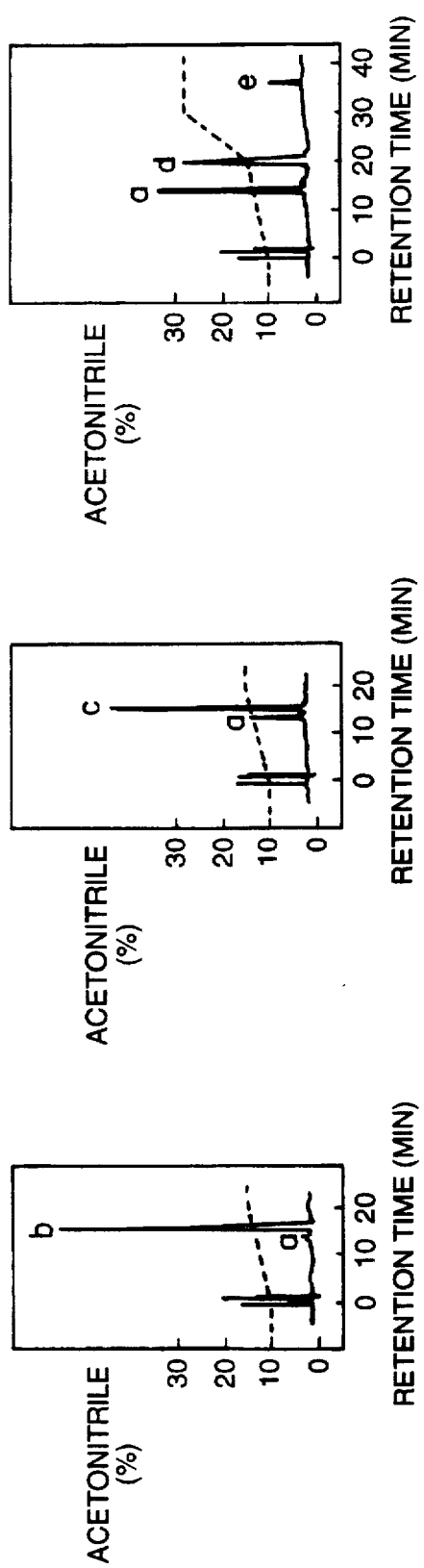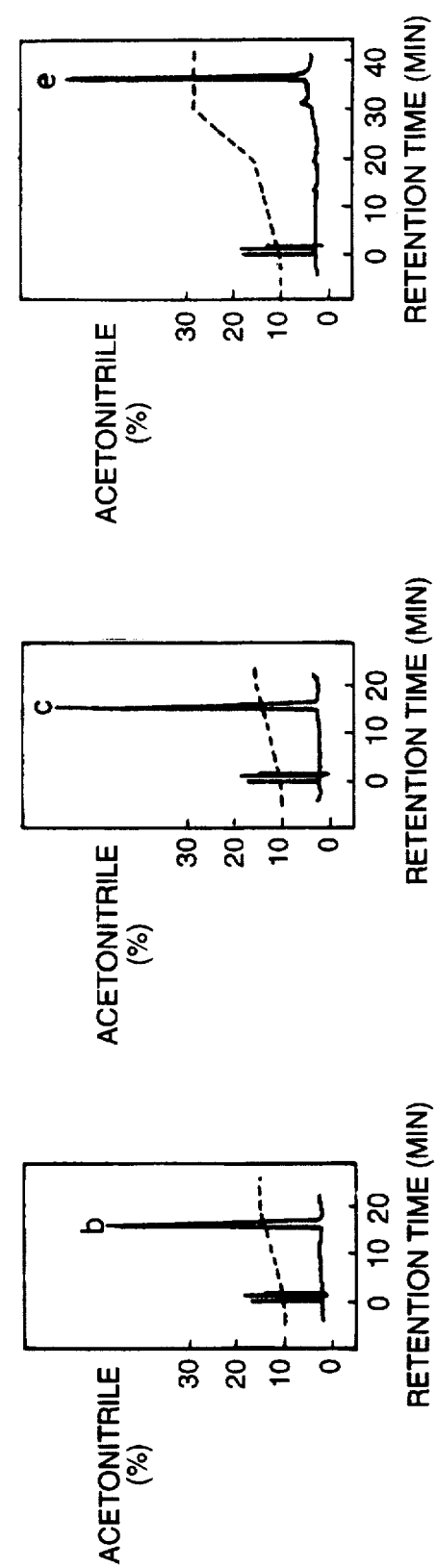

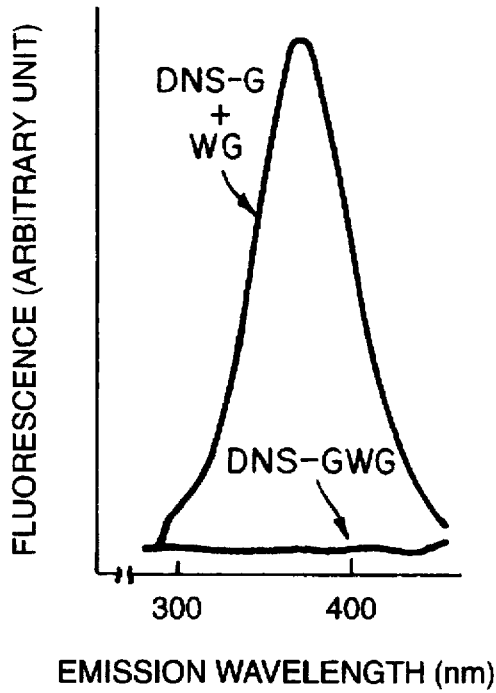
FIG._5a
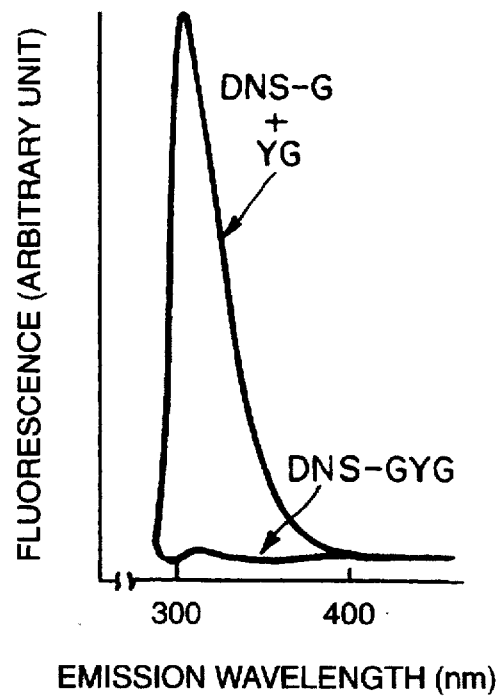
FIG._5b
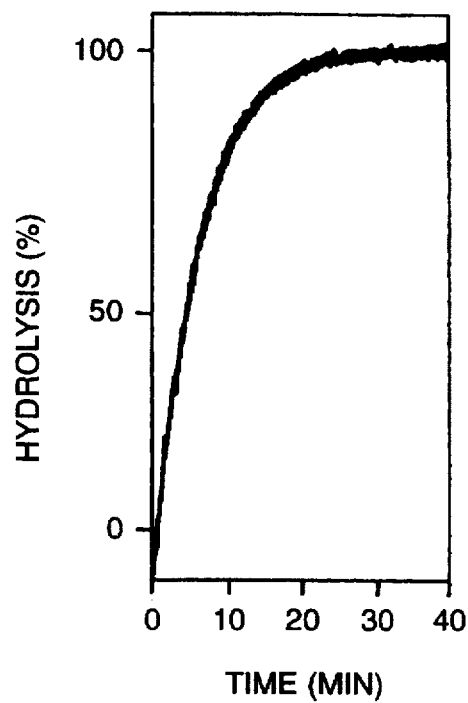
FIG._6a
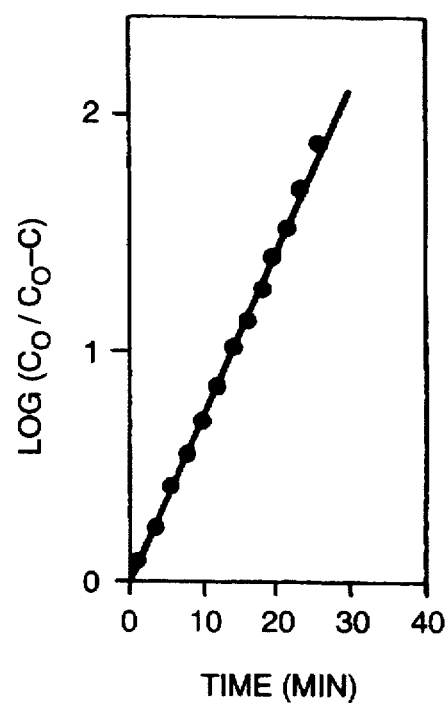
FIG._6b

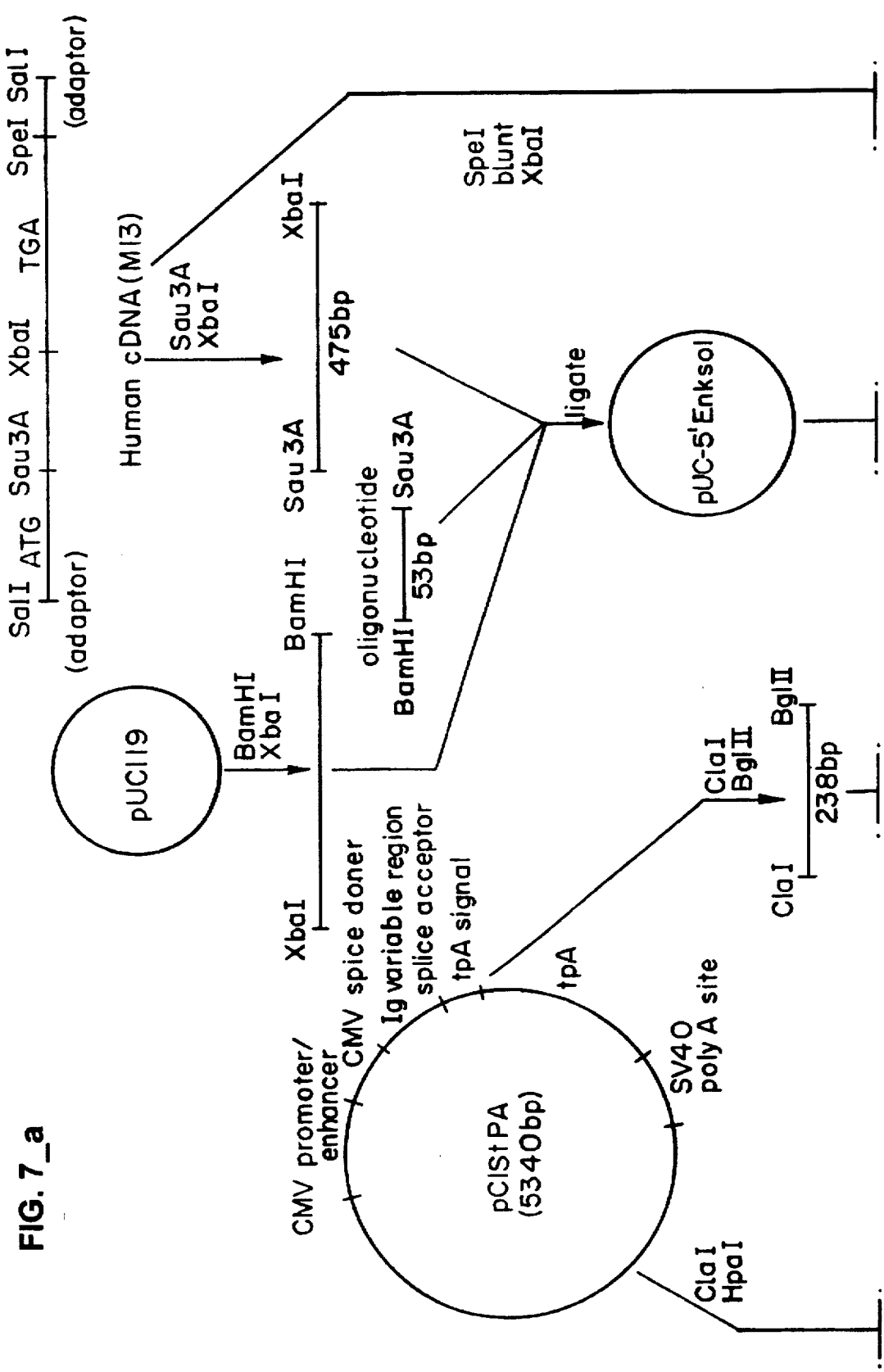
FIG. 7_a

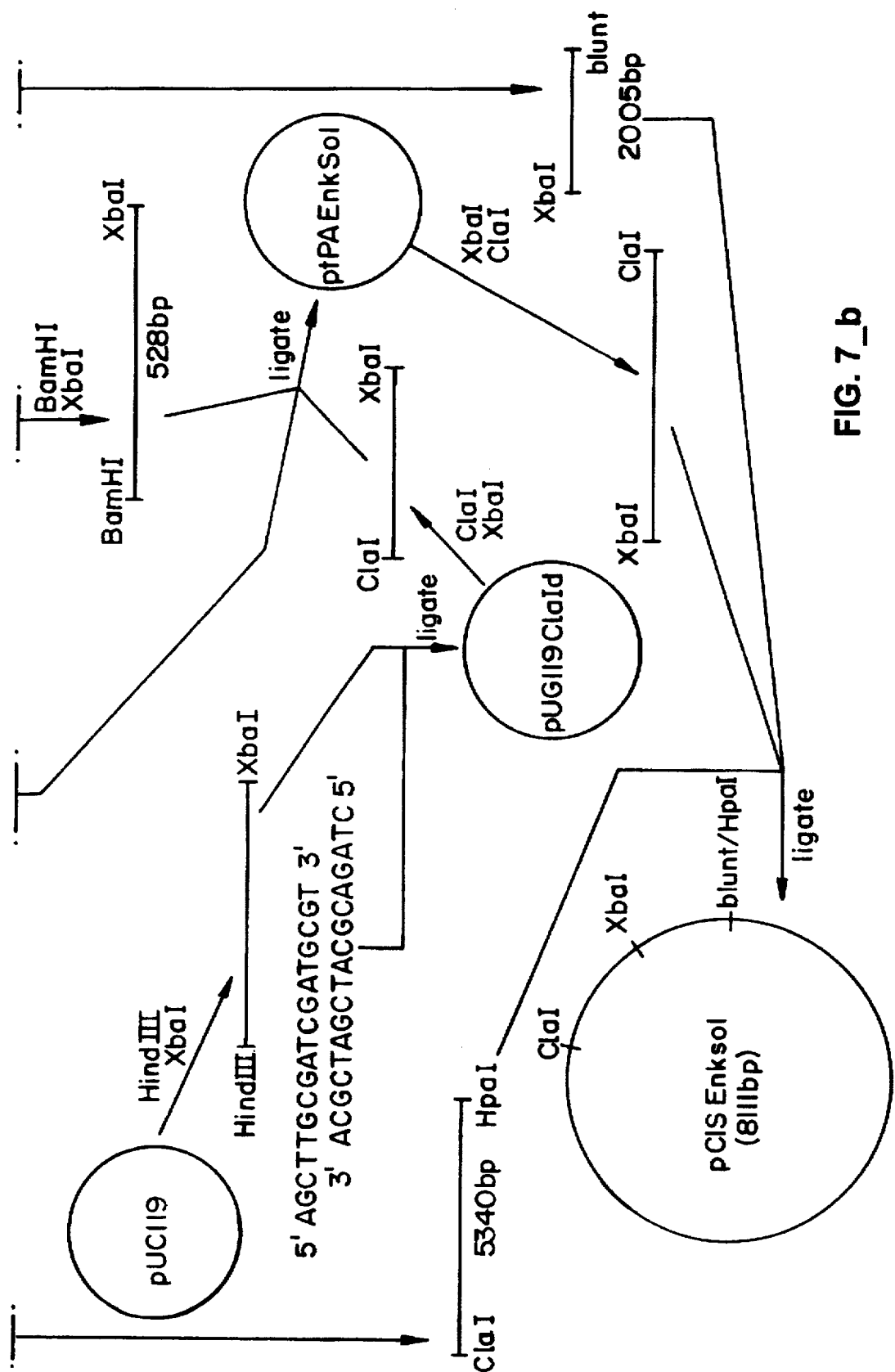
FIG. 7_b

COMPOSITIONS AND METHODS FOR THE SYNTHESIS AND ASSAY OF ENKEPHALINASE

This is a continuing application of U.S. Ser. No. 07/540,439, filed Jun. 19, 1990, now abandoned, which is a continuing application of U.S. Ser. No. 07/002,478, filed Jan. 12, 1987, now U.S. Pat. No. 4,960,700, which is a continuing application of U.S. Ser. No. 06/946,566, filed Dec. 24, 1986, now abandoned.

BACKGROUND OF THE INVENTION

This invention relates to enkephalinase, also known as neutral endopeptidase or kidney brush border neutral proteinase (E.C. 3.4.24.11, recommended name of the Enzyme Commission). The invention further relates to novel forms and compositions thereof and particularly to the means and methods for production of enkephalinase to homogeneity in therapeutically significant quantities. This invention also relates to preparation of isolated deoxyribonucleic acid (DNA) coding for the production of enkephalinase; to methods of obtaining DNA molecules which code for enkephalinase; to the expression of human and mammalian enkephalinase utilizing such DNA, as well as to novel compounds, including novel nucleic acids encoding enkephalinase or fragments thereof. This invention is also directed to enkephalinase derivatives, particularly derivatives lacking cytoplasmic and/or transmembrane portions of the protein, and their production by recombinant DNA techniques.

Enkephalinase has been purified from kidney (Kerr, M. A. and Kenny, A. J. Biochem. J. 137: 477–488 [1974], Gafford, J. et al., Biochemistry 22, 3265-3271 [1983] and Malfroy, B. and Schwartz, J. C., Life Sci. 31, 1745-1748 [1982]), intestine (Danielsen, E. M. et al., Biochem. J. 191, 545-548 [1980]), pituitary (Orlowski, M. and Wilk, S. Biochemistry 20: 4942-4945 [1981]), brain (Relton, J. M. et al., Biochem. J. 215: 755-762 [1983]) and lymph nodes (Bowes, M. A. and Kenny, A. J., Biochem. J. 236: 801-810 [1986]), and has been detected in many peripheral organs (Llorens, C. and Schwartz, J. C., Eur. J. Pharmacol. 69, 113-116 (1981) and in human neutrophils (Connelly, J. C. et al., Proc. Natl. Acad. Sci.[USA] 82: 8737-8741 [1985]). The distribution of enkephalinase in the brain closely parallels that of the enkephalins. Llorens, C. et al., J. Neurochem. 39: 1081-1089 (1982). Enkephalinase is also present in those peripheral tissues and cells that respond to and/or release various endogenous peptides. Enkephalinase is a membrane-bound glycoprotein with subunit $M_r$ values in the range of 87000 to 94000. Variation in the $M_r$ values are attributed to differences in the extent and pattern of glycosylation.

The substrate specificity of enkephalinase has been studied using the enzyme from rat and human kidney. Malfroy, B. and Schwartz, J. C., J. Biol. Chem. 259: 14365-14370 (1984); Gafford et al., Biochemistry 22: 3265-3271 (1983); and Pozsgay, M. et al., Biochemistry 25: 1292-1299 (1986). These studies indicate that enkephalinase preferentially hydrolyzes peptide bonds comprising the amino group of a hydrophobic residue, shows a marked preference for short peptides, and is most efficient when it acts as a dipeptidyl carboxypeptidase releasing a carboxy terminal dipeptide. Enkephalinase, which had been found in cerebral synaptic membranes, efficiently cleaves the $Gly^3$-$Phe^4$ amide of enkephalins (Malfroy, B. et al., Nature (Lond.) 276: 523-526 [1978]). Enkephalinase has also been found to cleave the heptapeptide $(Met^5)$enkephalin-$Arg^6$-$Phe^7$ (Schwartz, J. C. et al., In Proceedings International Union of Pharmacology 9th Congress of Pharmacology, 3: ed. by J. F. Mitchell et al., 277–283, McMillan Press Ltd., London, [1984]) as well as a variety of other neuropeptides, such as cholecystokinin (Zuzel, K. A. et al., Neuroscience 15: 149–158 [1985]), substance P (Horsthemke, B. et al. Biochem. Biophys. Res. Comm. 125: 728–733 [1984]), neurotensin (Checler et al., 1983), angiotensin I and angiotensin II (Matsas et al., Biochem J. 223: 433 [1984] and Gafford et al., Biochemistry 22: 3265 [1983]), kinins, e.g. bradykinin (Gafford, J. T. et al., Biochemistry 22: 3265-3271 [1983]), oxytocin (Johnson et al., 1984), and somatostatin (Mumford, R. A. et al., Proc. Natl. Acad. Sci. [USA] 78:6623-6627 [1981]). While enkephalinase is capable of hydrolyzing many biological peptides in vitro (Kenny, A. J. Trends in Biochem. Sci. 11: 40–42 [1986]), in vivo enkephalinase has to date only been implicated in the hydrolysis of endogenous enkephalins when released in brain (Schwartz, J. C. et al., Life Sciences 29: 1715–1740 [1981] and Lecomte, J. M. et al., J. Pharmacol. Exp. Ther. 237: 937–944 [1986]). Although the levels of enkephalinase in blood are normally very low (Connelly et al., supra) enkephalinase was found to be present in high levels in the serum from patients with adult respiratory distress syndrome (Connelly et al. Supra). Enkephalinase cleaves the chemotactic tripeptide fMet-Leu-Phe. Id. It was also observed that neutrophils from donors who smoked had enkephalinase activites about twice that of nonsmokers. Id. Enkephalinase has also been found in high levels in the microvilli of human placentae (Johnson, A. R. et al., Peptides 5: 789–796 [1984]).

Although the isolation of enkephalinase from various tissues has been described in the literature as shown above, the precise structure of enkephalinase has not been previously established. While some quantities of "purified" enkephalinase have been available as obtained from various tissues, the low concentration of enkephalinase in blood and tissues and the high cost, both economic and of effort, of purifying the protein from tissues makes this a scarce material. It is an object of the present invention to isolate DNA encoding enkephalinase and to produce useful quantities of human and mammalian enkephalinase using recombinant DNA techniques. It is a further object herein to prepare novel forms of enkephalinase. It is still another object herein to provide an improved substrate for the assay of enkephalinase activity. This and other objects of this invention will be apparent from the specification as a whole.

SUMMARY OF THE INVENTION

Objects of this invention have been accomplished by a method comprising: identifying and cloning the gene which codes for mammalian enkephalinase; incorporating that gene into a recombinant DNA vector; transforming a suitable host with the vector including that gene; expressing the mammalian enkephalinase gene in such a host; and recovering the mammalian enkephalinase that is produced. Similarly, the present invention makes it possible to produce human enkephalinase and/or derivatives thereof by recombinant techniques, as well as providing products and methods related to such human enkephalinase production. The isolation and identification of the enkephalinase gene was extremely difficult. The mRNA was rare and no cell line or other source of large quantities of mRNA was known, and heretofore no amino acid sequence for an enkephalinase was known.

The present invention is directed to the compositions and methods of producing mammalian enkephalinase via recombinant DNA technology, including: 1) the discovery and identity of the entire DNA sequence of the protein and the 5'-flanking region thereof; 2) the construction of cloning and expression vehicles comprising said DNA sequence, enabling the expression of the mammalian enkephalinase protein, as well as met, fusion or signal N-terminus conjugates thereof; and 3) viable cell cultures, genetically altered by virtue of their containing such vehicles and capable of producing mammalian enkephalinase polypeptide. This invention is further directed to compositions and methods of producing DNA which codes for cellular production of mammalian enkephalinase. Yet another aspect of this invention are new compounds, including deoxyribonucleotides and ribonucleotides which are utilized in obtaining clones which are capable of expressing enkephalinase. Still another aspect of the present invention is enkephalinase essentially free of all naturally occurring substances with which it is typically found in blood and/or tissues, i.e., the enkephalinase produced by recombinant means will be free of those contaminants typically found in its in vivo physiological milieu. In addition, depending upon the method of production, the enkephalinase hereof may contain associated glycosylation to a greater or lesser extent compared with material obtained from its in vivo physiological milieu, i.e. blood and/or tissue. This invention is further directed to novel enkephalinase derivatives, in particular derivatives lacking enkephalinase amino terminal residues, e.g. derivatives lacking the hydrophobic N-terminal amino acid sequence which constitutes the enkephalinase transmembrane domain.

The mammalian enkephalinase and derivatives thereof of this invention are useful in the treatment of various pathological disorders associated with various endogenous peptides such as the tachykinins, for example substance P. and the kinins, particularly bradykinin. The endogenous peptides may be associated with various pathological disorders including acute inflammation, hyperimmune responses e.g. anaphylaxis, tumors such as small cell lung cancer, carcinoid tumors, endocrine disorders, alterations in vascular permeability e.g. vasodilation attendant factor XII activation, and hypertension. Mammalian enkephalinase and its derivatives also are useful in diagnostic immunoassays for enkephalinase substrates such as bradykinin, wherein the enkephalinase serves to confirm the specificity of the assay for the substrate analyte by predigestion of an aliquot of the test sample. Finally, enkephalinase is useful as an immunosuppressant by virtue of its ability to digest chemotactic molecules. Other uses for enkephalinase will be apparent to those skilled in the art.

BRIEF DESCRIPTION OF THE DRAWINGS

FIG. 1 Nucleotide and amino acid sequence of human enkephalinase. The nucleotide sequence of the human enkephalinase mRNA was determined from DNA sequence analysis of a single clone. Predicted amino acids of the enkephalinase polypeptide are shown above the DNA sequence and are numbered from the first residue of the N-terminal of the analagous purified protein.

FIGS. 2a–2b FIGS. 2a–2b are collectively referred to herein as FIG. 2. Nucleotide and amino acid sequence of rat enkephalinase. The nucleotide sequence of the rat enkephalinase mRNA was determined from DNA sequence analysis of the cDNA clones λB16, λK3, λK5, λK2 and λB10 as shown in FIG. 2b. Predicted amino acids of the enkephalinase polypeptide are shown above the DNA sequence and are numbered from the first residue of the mature protein as determined by N-terminal protein sequencing. Alternate start codons are $Met^{-1}$ and $Met^{-8}$.

FIG. 3 SDS Polyacrylamide electrophoresis gel of purified rat kidney enkephalinase.

FIG. 4 HPLC analysis of the hydrolysis of tryptophan-containing peptides by purified rat kidney enkephalinase. The peptides (1 mM) were incubated for 1 hr at 37° C. with 5 ng purified rat kidney enkephalinase, without (A, B, C) and with A', B', C') 100 nM thiorphan. The substrates and fragments were resolved by reverse phase HPLC using a gradient of acetonitrile in 0.1% trifluoroacetic acid (dotted Line). A and A', Gly-Trp-Gly; B and B', N-Acetyl-Gly-Trp-Gly; C and C', dansyl-Gly-Trp-Gly. Peptides eluted are: a, Trp-Gly; b, Gly-Trp-Gly; c, N-Acetyl-Gly-Trp-Gly; d, dansyl-Gly; and e, dansyl-Gly-Trp-Gly.

FIG. 5 Characterization of the fluorescence transfer between tryptophan and dansyl in dansyl-Gly-Trp-Gly and tyrosine and dansyl in dansyl-Gly-Tyr-Gly.

Figure 8:
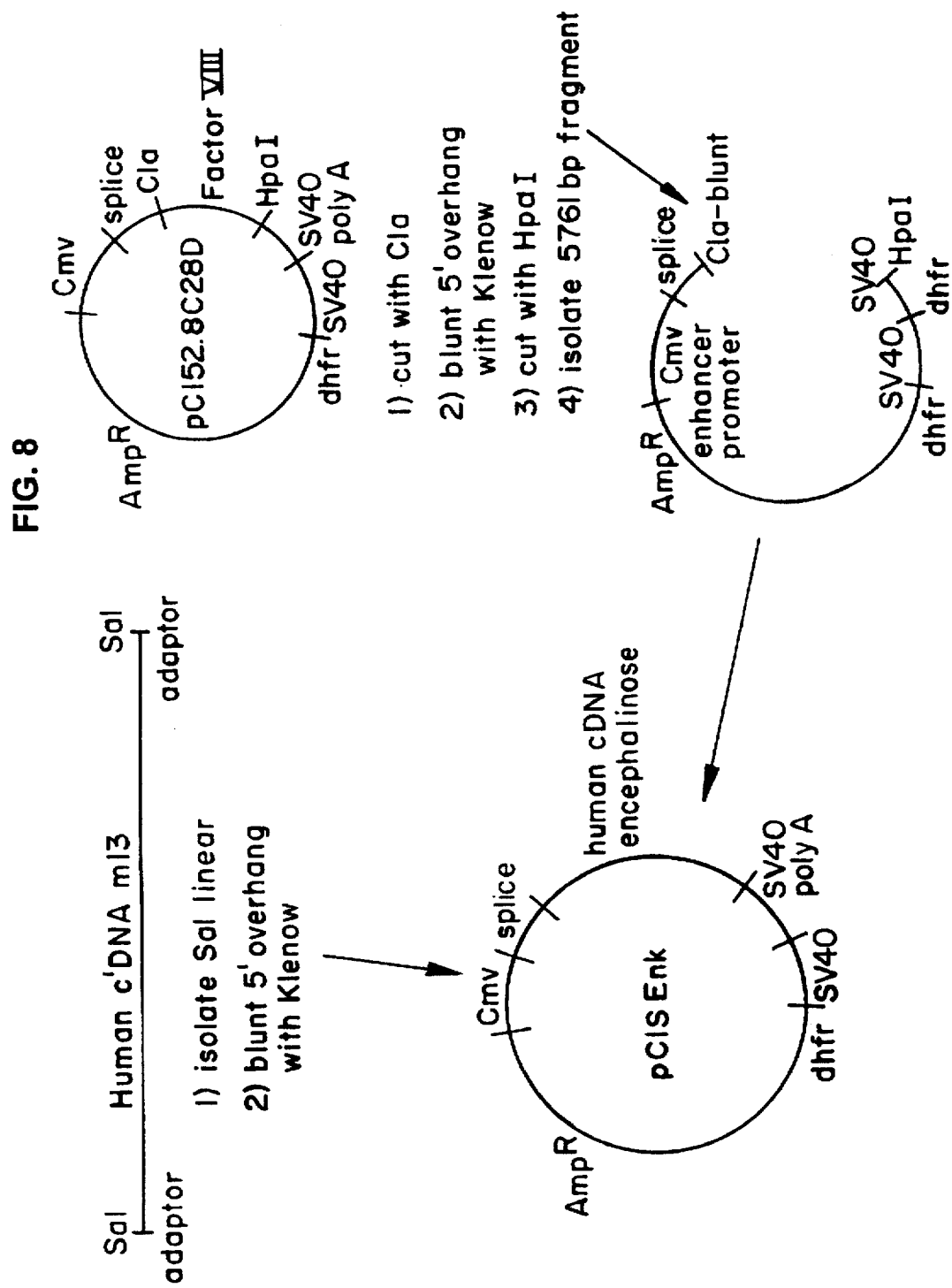

Fluorescence spectra were obtained using $10^{-4}$M peptides in water at 37° C. Excitation was set at 280 nm. Slits were 2 nm for both excitation and emission. The sensitivity of the fluorimeter was ten times higher for the tyrosine containing peptides than for tryptophan.

FIG. 6 Continuous fluorescence recording of the hydrolysis of dansyl-Gly-Trp-Gly by purified rat kidney enkephalinase. Purified rat kidney enkephalinase (350 ng) was added to 500 μl of dansyl-Gly-Trp-Gly ($5\times10^{-6}$M) in 50 mM HEPES buffer, pH 7.4, containing 0.1% Tween 20. Fluorescence (excitation 280 nm, emission 350 nm, slits set at 2 nm) was continuously recorded at 37° C. (a). The first order plot of substrate degradation (b) was obtained using measurements every 2 min, on the graph shown.

FIG. 7 A contemplated procedure for the construction of expression vectors for human enkephalinase deletional variants.

FIG. 8 A procedure for construction of an expression vector for full length human enkephalinase.

DETAILED DESCRIPTION

As used herein, enkephalinase or enkephalinase derivatives refers to proteins which are enzymatically active or are immunologically cross-reactive with enzymatically active enkephalinase. Enzymatically functional enkephalinase is capable of cleaving the $Gly^3$-$Phe^4$ amide bond of $^3$H-($DAla^2$, $Leu^5$)enkephalin in an assay as described by Llorens et al. (1982).

Included within the scope of enkephalinase as that term is used herein are enkephalinase having native glycosylation and the amino acid sequences of rat and human enkephalinase as set forth in FIG. 1 or 2, analogous enkephalinases from other animal species such as bovine, porcine and the like, deglycosylated or unglycosylated derivatives of such enkephalinases, amino acid sequence variants of enkephalinase and in vitro-generated covalent derivatives of enkephalinases. All of these forms of enkephalinase are enzymatically active or, if not, they bear at least one immune epitope in common with enzymatically-active enkephalinase.

Amino acid sequence variants of enkephalinase fall into one or more of three classes: Substitutional, insertional or deletional variants. These variants ordinarily are prepared by site specific mutagenesis of nucleotides in the DNA encoding the enkephalinase, thereby producing DNA encoding the variant, and thereafter expressing the DNA in recombinant cell culture. However, variant enkephalinase fragments having up to about 100–150 residues may be conveniently prepared by in vitro synthesis. Amino acid sequence variants are characterized by the predetermined nature of the variation, a feature that sets them apart from naturally occurring allelic or interspecies variation of the enkephalinase amino acid sequence. The variants typically exhibit the same qualitative biological activity as the naturally-occurr analogue, although variants also are selected in order to modify the characteristics of enkephalinase as will be more fully described below.

While the site for introducing an amino acid sequence variation is predetermined, the mutation per se need not be predetermined. For example, in order to optimize the performance of a mutation at a given site, random mutagenesis may be conducted at the target codon or region and the expressed enkephalinase variants screened for the optimal combination of desired activity. Techniques for making substitution mutations at predetermined sites in DNA having a known sequence are well known, for example M13 primer mutagenesis.

Amino acid substitutions are typically of single residues; insertions usually will be on the order of about from 1 to 10 amino acid residues; and deletions will range about from 1 to 30 residues. Deletions or insertions preferably are made in adjacent pairs. i.e. a deletion of 2 residues or insertion of 2 residues. Substitutions, deletions, insertions or any combination thereof may be combined to arrive at a final construct. Obviously, the mutations that will be made in the DNA encoding the variant enkephalinase must not place the sequence out of reading frame and preferably will not create complementary regions that could produce secondary mRNA structure (EP 75,444A).

Substitutional variants are those in which at least one residue in the FIG. 1 or 2 sequences has been removed and a different residue inserted in its place. Such substitutions generally are made in accordance with the following Table 1 when it is desired to finely modulate the characteristics of enkephalinase.

TABLE 1

| Original Residue | Exemplary Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in enkephalinase properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A major class of substitutional or deletional variants are those involving the transmembrane and/or cytoplasmic regions of enkephalinase. The cytoplasmic domain of enkephalinase is the sequence of amino acid residues commencing at either of two alternative start codons shown in FIG. 2 (Met$^{-8}$ or Met$^{-1}$ or in FIG. 1 (beyond residue Lys$^{-5}$ or Met$^{-1}$) and continuing for approximately 21—24 additional residues. In the rat and human sequence the Pro-Lys-Pro-Lys-Lys-Lys domain (residues at about 8 through 13) is believed to serve as a stop transfer sequence; the conformational bends introduced by the prolyl residues and the electropositive character provided by the lysyl residues act, together with the transmembrane region described below, to bar transfer of enkephalinase through the cell membrane.

The transmembrane region of enkephalinase is located in the rat sequence at about residues 21–44 (where Asp is +1 as shown in FIG. 2), and in the human sequence at the analogous location. This region is a highly hydrophobic domain that is the proper size to span the lipid bilayer of the cellular membrane. It is believed to function in concert with the cytoplasmic domains to anchor enkephalinase in the cell membrane.

Deletion or substitution of either or both of the cytoplasmic and transmembrane domains will facilitate recovery of recombinant enkephalinase by reducing its cellular or membrane lipid affinity and improving its water solubility so that detergents will not be required to maintain enkephalinase in aqueous solution. Deletion of the cytoplasmic domain alone, while retaining the transmembrane sequence, will produce enkephalinase which would be solubilized with detergent but which offers therapeutic advantages. The cytoplasmic domain-deleted enkephalinase will be more likely to insert into all membranes when administered as a therapeutic, thereby targeting its activity to the immediate extracellular envelope in which it is ordinarily active, and would improve its solubility in salve or liposomal compositions containing hydrophobic micelles. Preferably, the cytoplasmic or transmembrane domains are deleted, rather than substituted (for example [Ser]$_6$ for the stop transfer sequence), in order to avoid the introduction of potentially immunogenic epitopes.

The cytoplasmic and/or transmembrane (C-T) deleted or substituted enkephalinase can be synthesized directly in recombinant cell culture or as a fusion with a signal sequence, preferably a host-homologous signal. For example, in constructing a procaryotic expression vector the C-T domains are deleted in favor of the bacterial alkaline phosphatase, lpp or heat stable enterotoxin II leaders, and for yeast the domains are substituted by the yeast invertase, alpha factor or acid phosphatase leaders. In mammalian cell expression the C-T domains are substituted by a mammalian cell viral secretory leader, for example the herpes simplex gD signal. When the secretory leader is "recognized" by the host, the host signal peptidase is capable of cleaving a fusion of the leader polypeptide fused at its C-terminus to C-T deleted enkephalinase. The advantage of C-T deleted enkephalinase is that it is capable of being secreted into the culture medium. This variant is water soluble and does not have an appreciable affinity for cell membrane lipids, thus considerably simplifying its recovery from recombinant cell culture.

Substitutional or deletional mutagenesis is employed to eliminate N- or O-linked glycosylation sites. Alternatively, unglycosylated enkephalinase is produced in recombinant prokaryotic cell culture. Deletions of cysteine or other labile residues also may be desirable, for example in increasing the oxidative stability of the enkephalinase. Deletions or substitutions of potential proteolysis sites, e.g. Arg Arg, is accomplished by deleting one of the basic residues or substituting one by glutaminyl or histidyl residues.

Insertional amino acid sequence variants of enkephalinases are those in which one or more amino acid residues are introduced into a predetermined site in the target enkephalinase. Most commonly, insertional variants are fusions of heterologous proteins or polypeptides to the amino or carboxyl terminus of enkephalinase. Immunogenic enkephalinase derivatives are made by fusing an immunogenic polypeptide to the target sequence by cross-linking in vitro or by recombinant cell culture transformed with DNA encoding the fusion. Such immunogenic polypeptides preferably are bacterial polypeptides such as trpLE, beta-galactosidase and the like, together with their immunogenic fragments.

DNA encoding enkephalinase is obtained from other sources than rat or human by a) obtaining a cDNA library from the kidney of the particular animal, b) conducting hybridization analysis with labelled DNA encoding human enkephalinase or fragments thereof (usually, greater than 100 bp) in order to detect clones in the cDNA library containing homologous sequences, and c) analyzing the clones by restriction enzyme analysis and nucleic acid sequencing to identify full-length clones. If full length clones are not present in the library, then appropriate fragments may be recovered from the various clones and ligated at restriction sites common to the clones to assemble a full-length clone.

Enkephalinase derivatives that are not enzymatically active which fall within the scope of this invention include polypeptides that may or may not be substantially homologous with enkephalinase. These enkephalinase derivatives are produced by the recombinant or organic synthetic preparation of enkephalinase fragments or by introducing amino acid sequence variations into intact enkephalinase so that it no longer demonstrates enzyme activity as defined above. Only those non-enzymatically active enkephalinases or derivatives which exhibit immunological cross reactivity are included within the scope hereof.

Immunologically cross-reactive means that the candidate polypeptide is capable of competitively inhibiting the binding of an enzymatically-active enkephalinase with polyclonal antisera raised against the enzymatically-active analogue. Such antisera are prepared in conventional fashion by injecting goats or rabbits subcutaneously with the enzymatically-active analogue in complete Freund's adjuvant, followed by booster intraperitoneal or subcutaneous injections in incomplete Freunds.

Enkephalinase derivatives that are not enzymatically active but which are capable of cross-reacting with antisera to enzymatically-active enkephalinase are useful (a) as a reagent in diagnostic assays for enkephalinase or antibodies to enkephalinase, (b) when insolubilized in accord with known methods, as agents for purifying anti-enkephalinase antibodies from antisera or hybridoma culture supernatants, and (c) as immunogens for raising antibodies to enzymatically-active enkephalinase.

"Essentially free from" or "essentially pure" when used to describe the state of enkephalinase produced by the invention means free of protein or other materials normally associated with enkephalinase in its in vivo physiological milieu as for example when enkephalinase is obtained from blood and/or tissues by extraction and purification. Enkephalinase produced by the method of the instant invention was greater than or equal to 95% enkephalinase by weight of total protein; constituted a single saturated band (by Coomasie blue staining) on polyacrylamide gel electrophoresis; and had a specific activity of at least about 25 nmole/mg protein/min. using 20 nM of $^3$H-(DAla$^2$, Leu$^5$) enkephalin as substrate at 25° C. in 50 mM pH 7.4 HEPES buffer containing 0.02% Tween 20.

In general, prokaryotes are used for cloning of DNA sequences in constructing the vectors useful in the invention. For example, E. coli K12 strain 294 (ATCC No. 31446) is particularly useful. Other microbial strains which may be used include E. coli B and E. coli X1776 (ATCC No. 31537). These examples are illustrative rather than limiting.

Prokaryotes also are used for expression. The aforementioned strains, as well as E. coli W3110 (F$^-$, $\lambda^-$, prototrophic, ATTC No. 27325), bacilli such as Bacillus subtilus, and other enterobacteriaceae such as Salmonella typhimurium or Serratia marcescans, and various pseudomonas species may be used.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, E. coli is typically transformed using pBR322, a plasmid derived from an E. coli species (Bolivar, et al., Gene 2: 95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al., "Nature", 275: 615 [1978]; and Goeddel et al., "Nature" 281: 544 [1979]), alkaline phosphatase, the tryptophan (trp) promoter system (Goeddel "Nucleic Acids Res." 8: 4057 [1980] and EPO Appln. Publ. No. 36,776) and hybrid promoters such as the tac promoter (H. de Boer et al., "Proc. Natl. Acad. Sci. USA" 80: 21–25 [1983]). However, other functional bacterial promoters are suitable. Their nucleotide sequences are generally known, thereby enabling a skilled worker operably to ligate them to DNA encoding enkephalinase (Siebenlist et al., "Cell" 20: 269 [1980]) using linkers or adaptors to supply any required restriction sites. Promoters for use in bacterial systems also will contain a Shine-Dalgarno (S.D.) sequence operably linked to the DNA encoding enkephalinase.

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (Stinchcomb, et al., Nature 282: 39 [1979]; Kingsman et al., Gene 7: 141 [1979]; Tschemper et al., Gene 10: 157 [1980]) is commonly used. This plasmid already contains the trp1 gene which provides a selection marker for a mutant strain of yeast lacking the ability to grow in tryptophan, for example ATCC no. 44076 or PEP4-1 (Jones, Genetics 85: 12

[1977]). The presence of the trpl lesion as a characteristic of the yeast host cell genome then provides an effective environment for detecting transformation by growth in the absence of tryptophan.

Suitable promoting sequences for use with yeast hosts include the promoters for 3-phosphoglycerate kinase (Hitzeman et al., "J. Biol. Chem." 255: 2073 [1980]) or other glycolytic enzymes (Hess et al., "J. Adv. Enzyme Reg." 7: 149 [1968]; and Holland, "Biochemistry" 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

"Control region" refers to specific sequences at the 5' and 3' ends of eukaryotic genes which may be involved in the control of either transcription or translation. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence which may be the signal for addition of the poly A tail to the 3' end of the transcribed mRNA.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355–360 (1982). Of course, promoters from the host cell or related species also are useful herein.

Transcription of a DNA encoding enkephalinase by higher eukaryotes is increased by inserting an enhancer sequence into the vector. Enhancers are cis-acting elements of DNA, usually about from 10–300 bp, that act on a promoter to increase its transcription. Enhancers are relatively orientation and position independent having been found 5' (Laimins, L. et al., PNAS 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding enkephalinase. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol. Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred suitable host cells for expressing the vectors of this invention encoding enkephalinase in higher eukaryotes include: monkey kidney CV1 line transformed by SV40 (COS-7, ATCC CRL 1651); human embryonic kidney line (293, Graham, F. L. et al. J. Gen Virol. 36: 59 [1977]); baby hamster kidney cells (BHK, ATCC CCL 10); chinese hamster ovary-cells-DHFR (CHO, Urlaub and Chasin, PNAS (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383: 44–68 [1982]).

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform E. coli K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

"Transfection" refers to the taking up of an expression vector by a host cell whether or not any coding sequences are in fact expressed. Numerous methods of transfection are known to the ordinarily skilled artisan, for example, CaPO$_4$ and electro-poration. Successful transfection is generally recognized when any indication of the operation of this vector occurs within the host cell.

An assay using novel fluorescent substrates for enkephalinase was developed to assess whether enkephalinase is expressed. This assay is based on the disappearance of energy transfer between a tryptophan or a tyrosine residue and the 5-dimethylaminonaphthalene-1-sulfonyl group (dansyl) in the substrates dansyl-Gly-Trp-Gly or dansyl-Gly-Tyr-Gly upon hydrolysis of their Gly-Trp or Gly-Tyr amide bond by enkephalinase. No significant difference in Km or kcat values were found for dansyl-Gly-Trp-Gly and dansyl-Gly-Tyr-Gly as the active site of enkephalinase appears to accommodate tryptophan residues similarly to tyrosine. The tryptophan and tyrosine containing substrates can be used for continuous recording of enkephalinase activity.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8: 4057 (1980).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional. Maniatis, T. et al., *Molecular Cloning* pp. 133–134 (1982). Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T. et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 µg of the target DNA in 10 mM $MgCl_2$, 1 mM dithiothreitol, 50 mM NaCl, 10 mM Tris (pH 7.5) buffer at about 37° C. in the presence of 8 units of the Klenow fragment of DNA polymerase I and 250 µM of each of the four deoxynucleoside triphosphates. The incubation generally is terminated after 30 min. phenol and chloroform extraction and ethanol precipitation.

Enkephalinase and its recombinant expression product is obtained according to the following protocol:

1. Rat kidney enkephalinase was purified to apparent homogeneity.
2. The N-terminal amino acid sequence of enkephalinase was determined.
3. Purified enkephalinase was digested with Lysine C-proteinase. The peptides generated were resolved using HPLC over a C4 reverse phase column, and those peptides having a high absorbance at 280 nm were sequenced.
4. Oligonucleotide probes corresponding to a tryptophan-rich-containing peptide fragment were chemically synthesized.
5. cDNA libraries were constructed in λgt10, using a) randomly primed polyA$^+$ enriched mRNA from rat kidney, b) oligo dT primed polyA$^+$ enriched mRNA from rat brain, c) oligo dT primed polyA$^+$ enriched mRNA from rat kidney and d) oligo dT primed polyA$^+$ enriched mRNA from human placenta.
6. A pool of radiolabeled synthetic deoxyoligonucleotides complementary to codons for amino acid sequences of enkephalinase were used, as described below, such as:
   a) 5' GAA GTT GTT GGC GGA CTG CTG GGT CCA - CCA GTC GAC CAG GTC GCC
   b) 5' XTG XTG YGT CCA CCA ZTC 3'
      X=T or C
      Y=G, A, T, or C
      Z=A or G
7. The randomly primed rat kidney library was screened using the chemically synthesized oligonucleotide long and short probes labelled using polynucleotide kinase and $^{32}$P-ATP. Double positive plaques were purified and inserts sequenced.
8. One $^{32}$P labelled insert was used to rescreen the oligo dT primed rat brain and rat kidney libraries.
9. The complete reading frame for enkephalinase was obtained from two overlapping clones. The cDNA from kidney and brain were identical as determined by DNA sequence analysis of the clones obtained.
10. The human placental library was screened using a $^{32}$p-labelled partial clone from the rat cDNA. A full length clone, as determined by comparison to the rat cDNA, was isolated and sequenced.
11. A full length cDNA encoding rat enkephalinase was constructed from two overlapping clones in a plasmid and sequenced. It should be appreciated that disclosure of the DNA sequence in FIGS. 1 and 2 enables one to prepare extremely long probes having perfect homology with rat or human enkephalinase cDNA, thereby considerably simplifying and increasing the efficiency of probing cDNA or genomic libraries from these or other species, and making it possible to dispense with enkephalinase purification, sequencing, and the preparation of probe pools.
12. The full length cDNA encoding human enkephalinase was then tailored into an expression vehicle which was used to transform an appropriate host cell, which was then grown in a culture to produce the desired enkephalinase.
13. Biologically active mature enkephalinase produced according to the foregoing procedure has two alternative amino termini as shown in FIG. 2 which result in embodiments having 742 or 749 amino acids.

The following examples merely illustrate the best mode now known for practicing the invention, but should not be construed to limit the invention. All literature citations herein are expressly incorporated by reference.

EXAMPLE 1

Purification of Rat Kidney Enkephalinase

All the operations described below were performed at 4° C. The proteins were measured by the method of Bradford, M. M., Anal. Biochem. 72: 248–254 (1976) using bovine serum albumin as standard. The purification scheme adopted in this study was adapted from that of Malfroy and Schwartz, J. Biol. Chem. 259: 14365–14370 (1984) as follows:

The kidneys from sixty male rats (200–250 g) were removed and immediately frozen and stored at –20° C. until use.

Solubilization

The kidneys were thawed on ice, and homogenized into 1 liter of ice-cold HEPES (N-2-hydroxyethylpiperazine-N'-2'-ethanesulfonic acid) /NaOH buffer (50 mM, pH 7.4) using a Polytron homogenizer (5 minutes at maximal speed using the large probe of the homogenizer). The homogenate was centrifuged at 20,000 g for 30 minutes, the pellet resuspended using the Polytron homogenizer into 1 liter of the same buffer, and the suspension centrifuged again at 20,000 g for 30 minutes. The resulting pellet was then resuspended into 500 ml of the above buffer containing 0.1% Triton X-100, and left at 4° C. under constant magnetic stirring for 4 hours.

The suspension was centrifuged at 20,000 g for 1 hour, the supernatant discarded and the pellet resuspended into 500 ml of the above buffer, containing 1% Triton X-100 and left at 4° C. under magnetic stirring for 16 hours.

The suspension was centrifuged at 40,000 g for 1 hour, and the supernatant containing the solubilized enzyme was kept for further use. All the centrifugations were performed in a Sorvall RC-5B centrifuge, equipped with a GSA rotor, and a SS-34 rotor for the last step.

Concanavalin-A Chromatography

The solubilized preparation was loaded onto a 26×50 mm Concanavalin-A sepharose column (Pharmacia), equilibrated with 5 mM, pH 7.4 HEPES buffer containing 0.1% Triton X-100, at a flow rate of 100 ml/h. The column was washed with 500 ml of the above buffer, and the enzyme was eluted with 200 ml of buffer containing 500 mM methyl-alpha-D-glucopyranoside. This last fraction containing the enzyme was then subjected to DEAE Sephadex chromatography.

DEAE Sephadex A-50 Chromatography

The foregoing fraction eluted from the Concanavalin-A column was loaded at a flow rate of 100 ml/h onto a 16×100 mm DEAE Sephadex A-50 (Pharmacia) column previously equilibrated in 5 mM, pH 7.4 HEPES buffer, containing 0.1% Triton X-100. After an initial wash with 200 ml of the same buffer, the column was eluted at a flow rate of 50 ml/h with a 1 liter linear gradient of 0 to 250 mM NaCl in the same buffer. Fractions of ten ml were collected.

Hydroxylapatite Chromatography

The fractions containing enkephalinase activity absent of detectable angiotensin-converting enzyme (ACE) activity (as described by the method described by Malfroy, B. and Schwartz, J. C., J. Biol. Chem. 259: 14365-14370 [1984]) were pooled and loaded at a flow rate of 30 ml/h onto a 10 ×50 mm hydroxylapaptite column (BioRad) preequilibrated in 5 mM, pH 7.4 HEPES buffer, containing 0.1% Triton X-100. The column was eluted at a flow rate of 20 ml/hr. with a 400 ml linear gradient of 0 to 250 mM phosphate/Na ions in the above buffer. Fractions of eight ml were collected.

Concentration on Concanavalin-A Sepharose

The fractions eluted from hydroxylapatite containing enkephalinase activity were pooled and loaded at a flow rate of 10 ml/h onto a 10×10 mm Concanavalin-A sepharose column previously equilibrated with 5 mM, pH 7.4 Hepes buffer. The column was washed several times to dryness, i.e. until all buffer was absent, with the aforementioned buffer until no Triton X-100 could be detected in the eluate using the Bradford (1976) protein assay; then with the same buffer containing 500 mM methyl-alpha-D-glucopyranoside; and then several times with 1 ml 5 mM, pH 7.4 HEPES buffer containing 500 mM methyl-alpha-D-glucopyranoside and 0.1% Triton X-100, at a flow rate of 5 ml/h.

Superose Chromatography

One ml fractions obtained from the previous concanavalin-A step were concentrated to 200 µl using Centricon 30 devices and loaded onto a Superose-12 column (Pharmacia) equilabrated with 100 mM, pH 7.4 phosphate/Na buffer containing 1% SDS and 100 mM dithiothreitol. The column was eluted with the same buffer at a flow rate of 250 µl/min. Five hundred µl fractions were collected.

In another set of experiments, a Superose-6 column was used and run in 5 mM phosphate/Na buffer containing 150 mM NaCl and 0.1% Triton X-100, a buffer which allowed subsequent measurement of enkephalinase activity.

Assay of Enkephalinase Activity

Enkephalinase activity was measured as described by Llorens et al. (1982) using $^3$H-(DAla$^2$, Leu$^5$)enkephalin as a substrate. The buffer used was 50 mM, pH 7.4 Hepes, containing 0.02% Triton X-100.

Amino Acid Sequence Analysis

The fractions eluted from the Superose-6 column, containing enkephalinase activity and displaying a single protein band on polyacrylamide gels stained with coomassie blue, were used for sequence analysis. Enkephalinase was digested with Lysine-C proteinase in a ratio of 100 ng of proteinase for each 1 µg of enkephalinase. The peptide fragments generated were separated by HPLC on a Synchrom 2×100 mm C4 column, eluted with a linear gradient of 1 to 70% propanol-1 (1% per min) in 0.1% trifluoroacetic acid at a flow rate of 400 µl per minute. Peptides were detected by their absorbance at 214 and 280 nm. Sequential Edman degradation was performed on an Applied Biosystem, model 470A sequencer equipped with an on line model 120 PTH analyzer.

Six 1 ml fractions from the last Concanavalin-A step were collected and analyzed. The fractions contained a total of 525 µg protein, and enkephalinase activity at a specific activity of 27.4 nmole/mg protein/min, when measured at 25° C., using $^3$H-(DAla$^2$, Leu$^5$)enkephalin as a substrate. A 7.5% polyacrylamide SDS gel electrophoresis (FIG. 3) showed the presence of a 90 Kdalton protein, and of an approximately 50 Kdalton protein that was much less abundant. These two proteins could be easily separated by an additional chromatographic step on a Superose-6 or Superose-12 column. Only those fractions eluted from the Superose columns that contained the 90 Kdalton protein, also contained enkephalinase activity. This demonstrates that, in agreement with many previous reports, the molecular weight of enkephalinase is about 90 Kdaltons (for review see Kenny, cited above.) Fractions eluted from the Superose columns, and completely devoid of the 50 Kdalton contaminant protein, were used for protein sequencing.

Table 2 shows the N-terminal amino acid sequence. Sequencing was not extended over 15 cycles because the yields obtained were too low. The large size of enkephalinase could account for this difficulty.

TABLE 2

SEQUENCE ANALYSIS OF INTACT ENKEPHALINASE

| Cycle | Amino Acid | Yield (pmole) |
|---|---|---|
| 1 | (Asp) | 23.7 |
| 2 | Ile | 7.6 |
| 3 | Thr | 7.8 |
| 4 | Asp | 11.3 |
| 5 | Ile | 6.0 |
| 6 | Asn | 6.3 |
| 7 | Ala | 8.7 |
| 8 | Pro | 5.2 |
| 9 | Lys | 3.4 |
| 10 | Pro* | — |
| 11 | Lys* | — |
| 12 | Lys* | — |
| 13 | Lys* | — |
| 14 | Gln* | — |
| 15 | Arg* | — |

*Identified but not quantitated.

Other protein sequence data summarized in Table 3, were obtained after Lysine-C proteinase digest of enkephalinase, and HPLC purification of some of the peptides that were generated.

TABLE 3

| Peptide | Sequence (in order of cycle) |
|---|---|
| KC8 | (Leu) Leu Pro Gly Leu Asp Leu Asn His Lys |
| KC31 | (N.I.) Ile Thr Asp Ile Asn Ala Pro Lys Pro Lys* |
| KC2-12-6 | Glu Arg Ile Gly Tyr Pro Asp Asp Ile Ile Ser Asn - Glu Asn Lys |
| KC2-18-4 | (N.I.) Gly Asp Leu Val Asp Trp Trp Thr Gln Gln - Ser Ala Asn Asn Phe Lys* |
| KC2-19 | Glu Glu Glu Tyr Phe Glu Asn Ile Ile Gln Asn Leu Lys |
| KC2-32 | Ala Val Val Glu Asp Leu Ile Ala Gln Ile Arg Glu - Val Phe Ile Gln Thr Leu |

N.I. = not identified
*Identified but not quantitated

EXAMPLE 2

Enkephalinase DNA

Messenger RNA Isolation

Total RNA from rat kidney and brain was extracted by the guanidine thiocyanate method (Kaplan, B. B. et al., Biochem. J. 183, 181–4[1979]) and CsCl ultracentrifugation. The general strategy followed for identification of clones containing coding sequences for enkephalinase was as follows:

1. High complexity cDNA libraries were constructed in λgt10.
2. Both short and long probes were prepared.
3. cDNA clones were screened using both long and short probes and double positive plaques were isolated.

Library Construction

Polyadenylated mRNA was prepared from freshly obtained and liquid N₂ frozen rat kidneys (Kaplan et al., Biochem. J. 183:181–184 [1979]). High complexity cDNA libraries were constructed in λgt10 (Huynh et al., *DNA Cloning Techniques*, D. Clover, Ed., [1984]).

A rat kidney cDNA library was prepared using 5 ug poly A+ mRNA primed with either random octamer primers or with oligo dT primers. All cDNA libraries were constructed as described by Wood et al., Nature 312:330–337 (1984) except that the adaptors used had the sequence

5'-AATTCACTCGAGACGC-3'
3'GTGAGCTCTGCG-5'P.

This adaptor is referred to as EcoR1-XhoI. Other adaptors used were:

5'-AATTCGCATGGTCGACTAC-3'
GCGTACCAGCTGATG-5'P referred to as EcoRI-SalI:

5'-AATTCCTCGTGCTTCT-3'
GGAGCACGAAGA-5'P referred to as EcoRI.

In the case of the randomly primed library using the EcoRI-XhoI adaptor 6×10⁶ independent isolates of greater than 500 bp were obtained. In the case of the oligo dT primed library using an EcoRI adaptor 7×10⁵ isolates of greater than 1500 bp were obtained.

The foregoing procedure was followed for the preparation of a cDNA library from rat brain. An oligo dT primed library using an EcoRI-XhoI adaptor yielded 6×10⁶ independent isolates of greater than 1500 bp.

A similar procedure was followed for the preparation of a cDNA library from human placenta. An oligo dT primed library using an EcoRI-SalI adaptor yielded 7×10⁵ independent isolates of greater than 1500 bp. This library has previously been demonstrated to contain many full length cDNA clones (Ullrich, A. et al., 1985, Nature 313:756–761).

Preparation of DNA Probe

A total of seven lysine-C peptides were sequenced (Table 3) as well as the amino terminus (Table 2). Peptide KC2-18-4 containing two tryptophan residues was chosen to design oligonucleotide probes. A first probe (short probe) was a mixture of 18-mers that covered all the possible nucleotide sequences complementary to a gene coding for Asp-Trp-Trp-Thr-Gln-Gln, i.e. a mixture of 32 18-mers, as shown below:

Asp-Trp-Trp-Thr-Gln-Gln
coding strand: 5' GAX-TGG-TGG-ACY-CAA-CAA 3'
complementary: 5' XTG-XTG-YGT-CCA-CCA-ZTC 3'
  X=T or C
  Y=G, A, T, or C
  Z=G or A A second probe (long probe), complementary to a coding strand for the entire peptide KC2-18-4 (excluding the terminal Lys) was also used:

5' GAA GTT GTT GGC GGA CTG CTG GGT CCA CCA GTC GAC CAG GTC GCC 3'.

The oligonucleotide probes were labelled with ³²p using nucleotide kinase (Maniatis et al., Molecular Cloning, A Laboratory Manual [Cold Spring Harbor Laboratory, 1982]) and used to screen 5×10⁵ clones from a λgt10 library constructed by randompriming poly A-enriched rat kidney RNA. The library was plated at a density of 25,000 plaques per plate, lifted twice on nitrocellulose filters and the DNA on the filters was denatured and fixed as described by Maniatis et al. (1982).

The filters were prehybridized for 4 hours at room temperature in 50 mM sodium phosphate pH 6.8, 5× SSC (Blin et al., Nucleic Acids Res. 3:2303 [1976]), 150 mg/ml sonicated salmon sperm DNA, 5× Denhardt's solution (Wahl et al., Proc. Nat. Acad. Sci. [USA] 76:3683 [1979]) 20 percent formamide and then hybridized with 50× 10⁶ counts per minute of the labelled probes in the same solution. After an overnight incubation at room temperature, the filters were washed in 5× SSC, 0.1% SDS. The filters incubated with the long probe were then washed several times in 0.5× SSC, 0.1% SDS at room temperature. The filters incubated with the short probes pool were washed in 2× SSC containing 3M tetramethyl ammonium chloride (Wood et al., Proc. Natl. Acad. Sci. USA, 82: 1585–1588 [1985]) at 51° C. for 45 min., then in 2× SSC at room temperature for 1 hour. Filters were then exposed to Kodak XR-5 X-ray films with Dupont Lightning Plus intensifying screens for 16 hours at −70° C.

Two positive λgt10 phage were isolated and designated λK3 and λK4. The inserts of these were subcloned into M13 derivatives (Messing et al., "Nucl. Acids. Res." 9:309–321 [1981]) and sequenced by the dideoxy chain termination method of Sanger et al., Proc. Natl. Acad. Sci. USA 74:5463–5467 (1977).

This analysis revealed that neither of the characterized cDNAs contained sufficient sequence information to predict the complete structure of the protein. However, they did code for DNA comprising the peptide sequence of KC2-18-4. Therefore, rat kidney and rat brain oligo-dT primed libraries were screened.

The rat kidney library was screened with a suitable restriction fragment (both EcoRI fragments of λK3) from a previously analyzed cDNA and yielded several isolates (λK2 and λK5) of which none specified the remainder of the DNA sequences encoding the N-terminal region.

Similar screening of the rat brain library however gave two clones (λB16 and λB10), one of which, λB16, contained the N-terminal portion of the cDNA.

Completeness of the rat coding sequence was assessed from the presence of a long open reading frame which specified the sequence (as shown in FIG. 2) beginning with a start codon and preceded by an in-frame stop codon. An additional start codon is located 8 codons downstream. As noted, two possible initiation codons are present and either may be used. However, the N-terminal protein sequence suggests that the second start codon is actually used in vivo. Neither AUG codon conforms closely to the Kozak rule for prediction of initiation codons (Kozak, M., 1986, Cell 44: 283–292).

The cDNA inserts (see FIG. 2) were demonstrated to be the DNA coding for enkephalinase by comparing the amino acid sequence encoded by the cDNA with the peptide sequence, as described above, obtained from purified enkephalinase. The cDNA insert of these clones contains 912 bp of the 3' untranslated sequence and 78 bp at the 5' untranslated region.

At position 1917 in the rat DNA sequence, λB10 and λK2 have a T (coding for Asn). However, in λK3 a C was detected. This does not change the coding potential of the cDNA. Also, in the 3' untranslated sequence, position 2930 is a G in λK2 and an A in λB10. These different nucleotides may reflect a reverse transcriptase error.

Despite screening high complexity rat kidney and brain cDNA libraries, none yielded any full length cDNA's. This hampered initial screenings based on the use of two separate long probes such as those based on peptide sequences KC2-19 and KC2-32. Also the N-terminal probe was never found to be effective due to incorrect codon choices being made at the stage of design of the oligonucleotide. Screening with the KC2-18-4 short probe alone also was not successful in allowing isolation of positive clones because of the many false positives that were obtained with its use. Isolation of complete enkephalinase cDNA required dual screening with both long and short probes, whereas the typical procedure heretofore has been to use either screening method alone.

Human Enkephalinase cDNA

The cDNA insert of λK3 was used to screen $1.6 \times 10^6$ human placental cDNA clones as described above. Five positive clones were obtained, and two were sequenced. The largest insert obtained was three and a half Kilobases and yielded nearly a full length cDNA. As shown in FIG. 1, the entire human enkephalinase cDNA has been obtained based on the N-terminus of purified native enkephalinase. The predicted protein is greater than 90% homologous to the rat cDNA with several non-conservative changes being observed (French, S. and Robson, B., 1983, J. Mol. Evol. 19: 171–175).

At position 1413 in the human DNA sequence, one clone λH7 was observed to have a G. This codes for an Ala residue as shown in FIG. 1. However in a different clone λH5 this nucleotide is an A. This would change the codon to a Thr. Since the former is identical to the rat amino acid at position 465, the latter probably represents an error of reverse transcriptase synthesis of the mRNA.

EXAMPLE 3

Expression of Rat Enkephalinase

Partial cDNA clones encoding rat enkephalinase were obtained. Fusion of the appropriate fragments to construct a full length cDNA was undertaken as follows.

The M13 sequencing derivatives of λB16 and the 3' end of λK5 were used for these constructions. The full length λB16 insert of 1283 bp comprising 1269 bp cDNA and 14 bp of adaptor sequence was subcloned by digestion of the SalI sites in the adaptor and ligated to SalI cleaved M13tg130 for sequencing. This phage ss16X.1 was converted to double stranded DNA by primer extension (using the M13 universal sequencing primer and DNA polymerase) and digested with HindIII. HindIII cleaves the phage in the polylinker region 5' of the initiation codon. The HindIII site was blunted using T4 DNA polymerase. The plasmid was then digested with BglII (which is a unique site in rat enkephalinase located at position 1173) and the approximately 1195 bp (comprising 1173 bp cDNA and 17 bp of the polylinker and 56 bp of the adaptor) HindIII (blunted)BglII fragment isolated (fragment 1). The approximately 1397 bp (comprising 1368 bp of cDNA and 29 bp of the adaptor) EcoRI fragment of λK5, extending from the adaptor sequence located adjacent 5' of position 1190 in rat enkephalinase to the adaptor sequence located 3' of position 2457, was subcloned into M13mp19 for sequencing. This phage ssP5.1 was converted to double stranded DNA by primer extension, digested with EcoRI, blunt ended using T4 DNA polyperase and then digested with BglII. The approximately 1299 bp (comprising 1283 bp of cDNA and 16 bp from the adaptor) BglII-EcoRI (blunted) fragment was isolated (fragment 2).

Fragments 1 and 2 were ligated (in 10 mM rATP, which inhibits blunt-end ligation) and the approximately 2494 bp product (1195 bp+1299 bp=2494 bp) eluted from the gel. This approximately 2480 bp product was ligated to SmaI digested pSP64 (Melton, D. A. et al., Nucleic Acids Res. 12:7035–56 [1984]). This construct (p Rat. enk. antisense i.e. prENKanti) containing a full length rat enkephalinase was sequenced. prENKanti was cleaved with HindIII and SacI (both of these unique sites occur in the polylinker region of the pSP64 vector). This approximately 2537 bp fragment (comprising 2494 bp of fragments 1 and 2 plus 43 bp of the polylinker) is then used in the following procedure.

A) The fragment is ligated to pSP65 (Melton et al., Id.) cleaved with HindIII and SacI. The resultant plasmid prENKsense is used to generate in vitro transcription/translation product (using SP6 polymerase [Promega Biotech]) and rabbit reticulocyte lysate (Promega Biotech). This in vitro translated material is assayed for enkephalinase activity. In one assay only this material did not have detectable activity.

B) The 2537 bp fragment is blunted with T4 DNA polymerase and ligated to the pCIS2.8C28D described in U.S. patent application Ser. No. 06/907,297 which is hereby incorporated by reference which has been cleaved with ClaI and HpaI and blunted. pCIS2.8C28D is the same vector as pCIStPA, described below, except that it contains a factor VIII derivative instead of tPA. A recombinant plasmid pCISrENK was isolated in which the 5' end of the rat cDNA is located next to the CMV promoter enhancer region. This plasmid is expressed in human embryonic kidney (293) cells as described (see Example 4) and purified. This material was assayed using the assay described below, and shown to be biologically active.

EXAMPLE 4

Expression of Human Enkephalinase

These procedures are concerned with the construction of vectors containing the cytomegalovirus enhancer and promoter, the cytomegalovirus splice donor site and intron, the Ig variable region splice acceptor site, the SV40 polyadenylation and transcription site and cDNA encoding either cytoplasmic domain-deleted or cytoplasmic plus transmembrane (C-T) domain-deleted enkephalinase, either of which were ligated at their 5' ends to the tissue plasminogen activator secretion signal. The construction of the C-T deleted variant is shown in FIG. 7.

Cytoplasmic-Transmembrane Domains Deleted Enkephalinase

1) A 475 bp fragment is isolated from the full length human cDNA, described above, by digestion with Sau3A and XbaI. A 53mer is chemically synthesized having the following sequence:

```
5'-GA      TCC GGT ATT TGC AAG TCA TCA CAC TGC ATA AAA TCA GCT GCT-
3'          G CCA TAA ACG TTC AGT AGT CTG ACG TAT TTT AGT CGA CGA-
CGA CT                  3'
GCT GAC         TAG-5'.
```

This 53mer will comprise the amino terminus of the C-T deleted enkephalinase. The plasmid pUC119 (see for example U.S. patent application Ser. No. 06/907,297, which is hereby incorporated by reference) was digested with BamHI and XbaI. (In this regard, pUC19 can be employed in place of pUC119.) A three part ligation is then carried out. The 53mer is ligated to the 475 bp fragment and then the 528 bp fragment is cloned into pUC119 at the BamHI and XbaI sites. This intermediate plasmid, labelled pUC-5' Enksol, was sequenced to confirm proper orientation of the inserts.

2) pCIStPA (see U.S. patent application Ser. No. 06/907,185 which is hereby incorporated by reference) cloned in a dam⁻ strain of E.coli was digested with BgIII and ClaI. A 238 bp fragment containing the tPA signal sequence was isolated. pCIStPA also was cut with ClaI and HpaI and a 5340 bp fragment isolated. This 5340 bp fragment contains the CMV enhancer, promoter, splice site, Amp$^R$ gene, E. coli origin, SV40 DHFR and the SV40 poly A site.

3) pUC119 is digested with HindIII and XbaI to open the plasmid. The vector fragment is isolated and ligated to a HindIII-ClaI-XbaI adaptor oligonucleotide having the sequence as follows:

5' AGC TTG CGA TCG ATG CGT 3'
3' ACG CTA CGT ACG CAG ATC 5' the adaptor linked pUC119 plasmid (pUC119ClaId) is then digested with ClaI and XbaI to open the plasmid and the vector fragment isolated.

4) A three part ligation is then performed creating ptPAEnksol by ligating (a) the 238 bp fragment (ClaI-BgIII) from pCIStPA, (b) the 528 bp fragment (BamHI-XbaI) from pUC-5'Enksol, and (c) ClaI-XbaI digested pUC119ClaId vector fragment from step 3). This plasmid, ptPAEnksol is sequenced.

5) The full length human cDNA is cut with SpeI, the resulting 5' overhang is blunted using Klenow, and the cDNA then digested with XbaI. A 2005 bp fragment containing the 3' end of the enkephalinase cDNA was recovered. ptPAEnksol from step 4) is digested with ClaI and XbaI and a 766 bp fragment is recovered encoding the tPA signal fused to the amino terminal domain of C-T deleted enkephalinase. A 3 part ligation is performed with the 5340 bp vector fragment of pCIStPA and the 766 bp fragment from step 5). The recombinant plasmid pCIS-Enksol is isolated from a transformant colony and its sequence confirmed.

Cytoglasmic Domain-Deleted Enkephalinase

A 149mer is chemically synthesized having the following sequence:

brane domain-deleted enkephalinase is recovered from the culture of pCIS-Enksol transformants.

Full Length Human Enkephalinase

The full length human cDNA SalI fragment (including adaptor) is blunted using T4 DNA polymerase and ligated to pCIS2.8C28D which has been cleaved with HpaI and ClaI and blunted (FIG. 8). The recombinant plasmid, pCIShENK, (which has one cDNA encoding full length enkephalinase in the expression vector described above) is expressed in human embryonic kidney (293) cells and purified as described.

It should be appreciated that other suitable expression vectors are readily constructed by selection of suitable restriction sites and, if required, use of linkers or adaptors when inconvenient restriction sites are present. Also, partial digestions are conducted where required, i.e. where the designated fragments cannot be obtained under complete digestion conditions. Plasmid constructs are cloned in appropriate E. coli strains as will be known to those skilled in the art.

EXAMPLE 5

Assay for Detection of Enkephalinase

Enkephalinase activity has been measured using many different substrates, including tritiated enkephalins or analogs (Malfroy, B. et al., Nature 276: 523–526 |1978|, Schwartz, J. C. et al., Life Sci. 29: 1715–1740 |1981| and Llorens, C. et al., J.Neurochem. 39: 1081–1089 |1982|) and fluorescent substrates in two-step assays (Orlowski, M. and Wilk, S., Biochemistry 20, 4942–4950 |1981|). Florentin, C. et al., Anal. Biochem. 141: 62–69 |1984| recently designed a novel fluorescent substrate that allows continuous recording of enkephalinase activity. This assay is based on the occurrence of intramolecular quenching of dansyl fluorescence by a nitrophenyl group. The following method uses novel fluorescent enkephalinase substrates based on energy transfer that also allow continuous recording of the enzyme activity.

Synthesis of Substrates

The peptides were synthesized via solid phase methodology. Barany, C. and Merrifield, R. B. in The Peptides 2:1–284 (Gross, E. and Meienhofer, J., Eds., Academic Press, N.Y., 1980). The dansyl group was introduced with

| 5'-GA | TCC | TGG | ACT | CCA | CTG | GAG | ATC | AGC | CTC | TCG | GTC | CTT | GTC | CTG | CTC- |
|---|---|---|---|---|---|---|---|---|---|---|---|---|---|---|---|
| 3' | G | ACC | TGA | GGT | GAC | CTC | TAG | TCG | GAG | AGC | CAG | GAA | CAG | GAC | GAG- |
| CTC | ACC | ATC | ATA | GCT | GTG | ACA | ATG | ATC | CGA | CTC | TAT | GCA | ACC | TAC | GAT- |
| GAG | TGG | TAG | TAT | CGA | CAC | TGT | TAC | TAG | CGT | GAG | ATA | CGT | TGG | ATG | CTA- |
| GAT | GGT | ATT | TGC | AAG | TCA | TCA | GAC | TGC | ATA | AAA | TCA | GCT | GCT | CGA | CT - |
| CTA | CCA | TAA | ACG | TTC | AGT | AGT | CTG | ACG | TAT | TTT | AGT | CGA | CGA | GCT | GAC- |
| 3' | | | | | | | | | | | | | | | |
| TAG-5'. | | | | | | | | | | | | | | | |

This 149mer is ligated into the foregoing construction in place of the 53 bp oligonucleotide, resulting in pCIS-Enkinsol. This expression vector encodes cytoplasmic domain-deleted enkephalinase.

Human embryonic kidney line 293 (Graham et al., Id.) or CHO cells were transfected with either of pCIS-Enksol or pCIS-Enkinsol, stable transformants selected and, if desired, amplified in conventional fashion by use of the DHFR marker donated from pCIStPA. Cytoplasmic domain-deleted enkephalinase is recovered from the transformant culture of pCIS-Enkinsol transformants. Cytoplasmic and transmemdansyl chloride before the cleavage of the peptide from the resin support. After removal of the peptides from the support, purification was accomplished via preparative HPLC. Peptides were characterized by amino acid analysis and MNR.

Fluorometric Determination of the Hydrolysis of Dansylated Peptides

Fluorescence measurements were made using a Perkin Elmer, model 650-10S spectrofluorometer, equipped with a temperature controlled cell-holder, maintained at 37° C. Two procedures were used. The first combined a 50 μl solution of dansylated peptide with 50 μl of purified rat kidney enkephalinase in 50 mM, pH 7.4 HEPES buffer, containing 0.1% Tween 20, yielding a substrate concentration from 1 μM to 1 mM. After 1 hour at 37° C., 500 μl of 0.1M EDTA were added to the tubes. The 600 μl mixture was transferred into a quartz cuvette, and fluorescence measured. For dansyl-Gly-Trp-Gly, the excitation wavelength was set at 280 nm and emission at 360 nm. For the two tyrosine containing peptides, the excitation wavelength was at 277 nm and emission at 315 nm. Both slits were set at 2 nm. Known amounts of Trp-Gly and Tyr-Gly, diluted in the same mixture (100 μl HEPES, Tween 20, 500 μl EDTA), were run in parallel as standards. The fluorescence in the incubation media could thus be related to the amounts of hydrolyzed substrates. The second procedure permitted continuous monitoring of the hydrolysis of the dansylated peptides. A 500 μl solution of substrate at appropriate concentration, in 50 mM, pH 7.4 HEPES buffer containing 0.1% Tween 20 was pipetted in a quartz cuvette, and allowed to equilibrate in the cell holder of the fluorimeter at 37° C. Ten μl of purified rat kidney enkephalinase was added and the increase in tryptophan or tyrosine fluorescence was continuously monitored (excitation=280 nm, emission=360 nm for tryptophan, excitation 277, emission 315 for tyrosine). To minimize oxidation of tryptophan the intensity of excitation was reduced by adjusting the fluorimeter shutter so that a $10^{-4}$M solution of tryptophan in water gave a fluorescence of 20.0 with excitation set at 280 nm, emission at 360 nm, both slits at 2 nm, and sensitivity at 0.1. Under these conditions, tryptophan fluorescence was stable for over 2 hr.

When incubated with purified rat kidney enkephalinase, the peptides Gly-Trp-Gly, N-acetyl-Gly-Trp-Gly and dansyl-Gly-Trp-Gly were all hydrolysed at the Gly-Trp amide bond (FIG. 5). The unmodified tripeptide Gly-Trp-Gly was hydrolysed at a much lower rate than the two N-terminally substituted tripeptides. HPLC analysis demonstrated that the two peptides dansyl-Gly-Tyr-Gly and dansyl-Gly-Tyr-Gly-NH2 were hydrolysed at the Gly-Tyr amide bond. The hydrolysis of all substrates was completely inhibited when thiorphan was added in the reaction media.

The fluorescence spectrum of dansyl-Gly-Trp-Gly was dramatically modified when the Gly-Trp amide bond was hydrolysed. Upon excitation at 280 nm the emission spectrum of dansyl-Gly-Trp-Gly showed a maximum at 540 nm, with no fluorescence detectable at 350 nm. In contrast, under the same conditions, the emission spectrum of the peptides dansyl-Gly and Trp-Gly in equimolar concentration showed a maximum at 350 nm, and a complete disappearance of fluorescence at 540 nm. In a similar way, upon excitation at 277 nm, the emission spectrum of peptides dansyl-Gly-Tyr-Gly and dansyl-Gly-Tyr-Gly-NH2 showed a maximum at 540 nm, while the maximum was at 315 nm for a mixture of the peptides dansyl-Gly and Tyr-Gly or, dansyl-Gly and Tyr-Gly-NH2 (FIG. 6b). This change in emission spectrum is indicative of a fluorescence transfer between the tryptophan residue and the dansyl group in the peptide dansyl-Gly-Trp-Gly, or between the tyrosine residue and the dansyl group in the peptides dansyl-Gly-Tyr-Gly and dansyl-Gly-Tyr-Gly-NH2.

When dansyl-Gly-Trp-Gly was incubated with purified rat kidney enkephalinase and under excitation at 280 nm, the hydrolysis of the Gly-Trp amide bond of the substrate induced an increase in fluorescence intensity at 350 nm, which could be continuously recorded. Similarly, the hydrolysis of peptides dansyl-Gly-Tyr-Gly and dansyl-Gly-Tyr-Gly-NH2 could be continuously recorded by following the increase in fluorescence intensity at 315 nm under excitation at 277 nm.

The kinetic parameters for the hydrolysis of dansyl-Gly-Trp-Gly, dansyl-Gly-Tyr-Gly and Dansyl-Gly-Tyr-Gly-NH2 by purified rat kidney enkephalinase were measured by incubating increasing concentrations of the substrates with the enzyme and stopping the reaction by the addition of EDTA before fluorescence measurements were taken (Table 4). Because tryptophan fluorescence increases with pH, the use of EDTA to stop the reactions resulted in an enhanced sensitivity in the assay when dansyl-Gly-Trp-Gly was used as the substrate.

TABLE 4

Kinetic parameters for the hydrolysis of various substrates by purified rat kidney enkephalinase

| Substrate | $K_m$ (μM) | kcat (min$^{-1}$) | kcat/$K_m$ (μM$^{-1}$ min$^{-1}$) |
|---|---|---|---|
| $P_2 P_1 P'_1 P'_2$ | | | |
| I Gly-Trp-Gly | | 53 | |
| II N-acetyl-Gly-Trp-Gly | | 218 | |
| III dansyl-Gly-Trp-Gly | 30 | 902 | 30 |
| IV dansyl-Gly-Tyr-Gly | 41 | 1143 | 28 |
| V dansyl-Gly-Tyr-Gly-NH$_2$ | 90 | 248 | 3 |

$K_m$ and kcat values for substrates III, IV and V were obtained by measuring the increase in tryptophan or tyrosine fluorescence after 1 hr. incubations of increasing concentrations of substrates (from 1 μM to 1 mM) with 1 ng purified enzyme at 37° C. The kcat values for these substrates and peptides I and II were also obtained by HPLC analysis of 1 hr. incubations of 1 mM peptides with 200 ng (substrate I), 50 ng (substrates II and V), or 10 ng (substrates III and IV) enzyme. The kcat values obtained by both methods for substrates III, IV and V were in close agreement.

The specificity constant (kcat/$K_m$) of dansyl-Gly-Tyr-Gly-NH2 was much lower than that of the corresponding free carboxylic acid substrate dansyl-Gly-Tyr-Gly. This decrease in specificity constant was due both to an increased Km value and a decrease in kcat (Table 4).

EXAMPLE 6

Chemotactic Assay

The normal functions of mature neutrophils are chemotaxis, phagocytosis, microbicidal action, and digestion of foreign material. Chemotactic factors are generated at the site of inflammation which attract various immunological cells including neutrophils to that site. The mechanism underlying the chemotactic attraction of neutrophils to the inflammatory site is not fully understood. Enkephalinase has been implicated in the mechanism. Connelly, J. C. et al., Proc. Natl. Acad. Sci. (USA) 82, 8737–8741 (1985). In certain cases of hyperimmune responses abnormal influx of neutrophils and other immune cells may cause additional tissue damage.

Enkephalinase has been found to be bound to the cell membrane of human neutrophils. Connelly, et al., supra. Membrane bound enkephalinase from neutrophils cleaves the chemotactic peptide fMet-Leu-Phe. (Id.) Neutrophil degranulation and chemotaxis require cleavage of chemotactic peptides (Smith, R. et al., Fed. Proc. Fed. Am. Soc. Exp. Biol. 44, 576 [1985]) and Aswanikumar, S. et al., Proc. Natl. Acad. Sci. (USA) 73, 2439–2442 [1976]). Thus, it has been suggested that neutrophil membrane bound enkephalinase may be associated with the chemotactic signal by cleaving fMet-Leu-Phe in the immediate vicinity of the neutrophil receptor. This degradation would control the local concentration of the chemotactic peptide.

An assay was used to test the effects of enkephalinase on neutrophil chemotaxis. See U.S. patent application Ser. No. 06/707,005. Neutrophils were isolated by sedimentation over dextran from peripheral blood of human donors. A sample of neutrophils is placed over a 5 μm filter in a chemotaxis chamber containing aliquots of test material. Three to six replicates were run for each test for 1 hr. at 37° C. The number of migrating neutrophils in each chamber is then counted. The chemotactic potential is evaluated by the number of cells in five selected unit areas. A commercially available chemotaxis kit, Neuroprobe, Cabin John, Md. was used. Various specific inhibitors of enkephalinase were used to determine the role of enkephalinase in chemotaxis of neutrophils. Chemotactic activity is reported as the total number of neutrophils observed in five fields of the kit membrane under 100× magnification. Thus, the larger the number the more chemotactic was a particular test composition.

TABLE 5

Chemotactic Activity

|  | Neutrophil Migration (% control) |
| --- | --- |
| Formyl Met-Leu-Phe 1 μM | 100 |
| Formyl Met-Leu-Phe + Thiorphan 10 μM | 29 ± 19 (n = 5) |
| Formyl Met-Leu-Phe + Phosphoramidon 10 μM | 65 (n = 1) |

Thus, neutrophil enkephalinase modulates chemotactic activity.

Pharmaceutical Compositions

The compounds of the present invention can be formulated according to known methods to prepare pharmaceutically useful compositions, whereby the enkephalinase product hereof is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration to the host.

The enkephalinase hereof is administered for example to subjects suffering from kinin-mediated diseases or disorders in order to neutralize excessive bradykinin. In hypovolemic sequelae of hyperimmune reactions sterile enkephalinase is administered intravenously at dosages sufficient to resolve the hypovolemia as is readily determined by the clinician.

We claim:

1. Water soluble mammalian neutral endopeptidase which is free of detergent, wherein said neutral endopeptidase is encoded by a DNA selected from the group consisting of:
    a) a rat DNA sequence encoding neutral endopeptidase,
    b) a human DNA sequence encoding neutral endopeptidase, and
    c) a DNA sequence which hybridizes to a) or b) and which encodes a mammalian neutral endopeptidase.

2. A non-naturally occurring neutral endopeptidase wherein a predetermined amino acid residue is substituted, inserted or deleted, wherein said variant neutral endopeptidase is encoded by a DNA which hybridizes to a rat DNA sequence encoding neutral endopeptidase or a human DNA sequence encoding neutral endopeptidase.

3. The neutral endopeptidase of claim 2 that is human neutral endopeptidase.

4. The neutral endopeptidase of claim 2 which cleaves the Gly-Trp or Gly-Tyr amide bond of the substrates dansyl-Gly-Trp-Gly or dansyl-Gly-Tyr-Gly.

5. Transmembrane domain-deleted mammalian neutral endopeptidase, wherein said transmembrane domain-deleted neutral endopeptidase is encoded by a DNA which will hybridize to a DNA sequence selected from the group consisting of:
    a) a rat DNA sequence encoding neutral endopeptidase; and
    b) a human DNA sequence encoding neutral endopeptidase.

6. Cytoplasmic domain-deleted mammalian neutral endopeptidase, wherein said cytoplasmic domain-deleted neutral endopeptidase is encoded by a DNA which will hybridize to a DNA sequence selected from the group consisting of:
    a) a rat DNA sequence encoding neutral endopeptidase, and
    b) a human DNA sequence encoding neutral endopeptidase.

7. Mammalian neutral endopeptidase according to claim 6 wherein the transmembrane domain is also deleted.

8. Human transmembrane domain-deleted neutral endopeptidase wherein said human transmembrane domain-deleted neutral endopeptidase is encoded by a DNA which will hybridize to a human DNA sequence encoding neutral endopeptidase.

9. The human neutral endopeptidase of claim 8 wherein the cytoplasmic domain is also deleted.

10. A neutral endopeptidase encoded by a DNA which hybridizes to a rat DNA sequence encoding neutral endopeptidase or a human DNA sequence encoding neutral endopeptidase and which encodes a mammalian neutral endopeptidase containing a deletion, insertion or substitution in the cytoplasmic domain.

11. A neutral endopeptidase encoded by a DNA which hybridizes to a rat DNA sequence encoding neutral endopeptidase or a human DNA sequence encoding neutral endopeptidase and which encodes a mammalian neutral endopeptidase containing a deletion, insertion or substitution in the transmembrane domain.

12. A pharmaceutical preparation useful for therapeutic treatment of endogenous peptide-mediated disorders or diseases comprising a therapeutically effective amount of neutral endopeptidase and a pharmaceutically acceptable carrier, wherein said neutral endopeptidase is encoded by a DNA selected from the group consisting of:
    a) a rat DNA sequence encoding neutral endopeptidase,
    b) a human DNA sequence encoding neutral endopeptidase, and
    c) a DNA sequence which hybridizes to a) or b) and which encodes a mammalian neutral endopeptidase.

13. The preparation of claim 12 which is sterile.

14. The preparation of claim 12 wherein the neutral endopeptidase is transmembrane domain-deleted neutral endopeptidase.

15. The pharmaceutical composition according to claim 12 wherein said neutral endopeptidase is human neutral endopeptidase.

16. The preparation of claim 12 wherein the neutral endopeptidase is cytoplasmic domain-deleted neutral endopeptidase.

17. The preparation of claim 16 wherein the carrier is a salve for epidermal application.

18. The pharmaceutical composition of claim 12 wherein both the amino terminal transmembrane domain and the cytoplasmic domain of said neutral endopeptidase are deleted.

19. The pharmaceutical composition according to claim 18 wherein said neutral endopeptidase is human neutral endopeptidase.

20. A composition comprising mammalian neutral endopeptidase unaccompanied by associated native glycosylation and which is free of glycosylated mammalian neutral endopeptidase, wherein said neutral endopeptidase is encoded by a DNA selected from the group consisting of:

a) a rat DNA sequence encoding neutral endopeptidase, b) a human DNA sequence encoding neutral endopeptidase, and c) a DNA sequence which hybridizes to a) or b) and which encodes a mammalian neutral endopeptidase.

* * * * *